US010544213B2

United States Patent
Grimm et al.

(10) Patent No.: US 10,544,213 B2
(45) Date of Patent: Jan. 28, 2020

(54) COMPOUNDS CAPABLE OF ANTAGONIZING ISLET AMYLOID POLYPEPTIDE (IAPP) INDUCED BETA-CELL DAMAGE AND IMPAIRED GLUCOSE TOLERANCE

(71) Applicants: Neurimmune Holding AG, Schlieren (CH); University of Zurich, Zurich (CH)

(72) Inventors: Jan Grimm, Dübendorf (CH); Fabrice Heitz, Bartenheim (FR); Fabian Wirth, St. Gallen (CH); Tobias Welt, Zurich (CH)

(73) Assignees: Neurimmune Holding AG, Schlieren (CH); University of Zurich, Zurich (CH)

( * ) Notice: Subject to any disclaimer, the term of this patent is extended or adjusted under 35 U.S.C. 154(b) by 470 days.

(21) Appl. No.: 15/125,450

(22) PCT Filed: Mar. 12, 2015

(86) PCT No.: PCT/EP2015/055238
§ 371 (c)(1),
(2) Date: Sep. 12, 2016

(87) PCT Pub. No.: WO2015/136055
PCT Pub. Date: Sep. 17, 2015

(65) Prior Publication Data
US 2018/0179276 A1    Jun. 28, 2018

(30) Foreign Application Priority Data

Mar. 12, 2014  (EP) .................... 14159194

(51) Int. Cl.
| C07K 16/18 | (2006.01) |
| A61K 45/06 | (2006.01) |
| C07K 16/26 | (2006.01) |
| A01K 67/027 | (2006.01) |
| A61K 47/68 | (2017.01) |
| A61P 3/10 | (2006.01) |
| A61K 39/395 | (2006.01) |
| A61K 49/00 | (2006.01) |
| A61K 39/00 | (2006.01) |

(52) U.S. Cl.
CPC .......... *C07K 16/26* (2013.01); *A01K 67/0275* (2013.01); *A61K 39/3955* (2013.01); *A61K 45/06* (2013.01); *A61K 47/6847* (2017.08); *A61K 49/0008* (2013.01); *A61P 3/10* (2018.01); *A01K 2217/052* (2013.01); *A01K 2227/105* (2013.01); *A01K 2267/0362* (2013.01); *A61K 2039/505* (2013.01); *C07K 2317/21* (2013.01); *C07K 2317/24* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

2013/0071401 A1   3/2013  Bram et al.
2016/0376354 A1*  12/2016  Grimm ............ C07K 14/4711
                                                           424/133.1

FOREIGN PATENT DOCUMENTS

| JP | 2008517885 A | 5/2008 |
| WO | WO-2011/151833 A1 | 12/2011 |
| WO | 2012170977 A1 | 12/2012 |
| WO | WO-2014/041069 A1 | 3/2014 |
| WO | WO-2015/004632 A1 | 1/2015 |

OTHER PUBLICATIONS

Paul, Fundamental Immunology, (textbook), 292-295,1993.*
Rudikoff et al (Proc Natl Acad Sci USA, 79: 1979, 1982).*
MacCallum et al. (J. Mol. Biol. 262:732-745, 1996).*
Vajdos et al (J Mol Biol 320: 415-428, 2002).*
Wu et al (J Mol Biol 294: 151-162, 1999).*
Butler et al (Diabetes 53: 1509-1516, 2004).*
Yan et al (PNAS 103: 2046-2051, 2006).*
Hoppener et al (Diabetologia 42: 427-434, 1999).*
Kipriyanov et al (Mol Biotech 26: 39-60, 2004).*
De Pascalis et al. (The Journal of Immunology 169: 3076-3084, 2002).*
Bram et al., "Apoptosis induced by islet amyloid polypeptide soluble oligomers is neutralized by diabetes-associated specific antibodies," Sci Rep. 4:4267 (2014) (9 pages).
Gurlo et al., "Evidence for proteotoxicity in beta cells in type 2 diabetes: toxic islet amyloid polypeptide oligomers form intracellularly in the secretory pathway," Am J Pathol. 176(2):861-9 (2010).
Matveyenko et al., "Beneficial endocrine but adverse exocrine effects of sitagliptin in the human islet amyloid polypeptide transgenic rat model of type 2 diabetes: interactions with metformin," Diabetes. 58(7):1604-15 (2009).
International Search Report and Written Opinion for International Patent Application No. PCT/EP2015/055238, dated Aug. 19, 2015 (16 pages).

(Continued)

*Primary Examiner* — Daniel E Kolker
*Assistant Examiner* — Aditi Dutt
(74) *Attorney, Agent, or Firm* — McDermott Will & Emery LLP; Kristina Bieker-Brady

(57) ABSTRACT

Described are molecules specifically binding to human islet amyloid polypeptide (hIAPP) also known as amylin, particularly human-derived antibodies as well as fragments, derivatives and variants thereof for antagonizing islet amyloid polypeptide (IAPP) induced β-cell damage and impaired glucose tolerance which are symptoms typically associated with diabetes mellitus type 2 (T2D).

24 Claims, 10 Drawing Sheets

Specification includes a Sequence Listing.

(56) References Cited

OTHER PUBLICATIONS

International Preliminary Report on Patentability for International Patent Application No. PCT/EP2015/055238, dated Sep. 13, 2016 (10 pages).
Janson, J. et al., "Spontaneous diabetes mellitus in transgenic mice expressing human islet amyloid polypeptide", Proc. Natl. Acad. Sci. USA., vol. 93, pp. 7283-7288, Jul. 1996.
World Health Organization (2018) Diabetes Programme, Intermediate States of Hyperglycemia, Retrieved on Jan. 24, 2019 from URL: https://www.who.int/diabetes/action_online/basics/en/index2.html (2 pages). [online].
Diabetes.co.uk, Impaired Glucose Tolerance, Retrieved on Jan. 24, 2019 from URL: https://www.diabetes.co.uk/impaired-glucose-tolerance.html (2 pages). [online].

* cited by examiner

NI-203.26C11-VH (variable heavy chain sequence VH) (SEQ ID NO: 2)

```
FR1----------------------CDR1--------FR2-----------CDR2------------
QVQLQESGPGLVKPSQTLSLTCTVSGGSISSGNYYWTWIRQPAGKGLEWIGHIYSSGTTNYNPSLES

FR3-------------------------------CDR3-------FR4--------
RVTISVDTSKNQFSLSLNSVTAADTAVYYCARPLATVPDAFNIWGQGTMVTVSS
```

NI-203.26C11-VK (variable light chain sequence VK) (SEQ ID NO: 4)

```
FR1--------------------CDR1----------FR2------------CDR2---FR3----
EIVMTQSPDSLAVSLGERATIKCKSSQSVLYSNKNFLAWYQQKPGQPPKLLIYWASTRESGVPDRFS

------------------------CDR3-----FR4-------
GSGSGTDFTLTISSLQAEDVAVYYCQQYYSNPNTFGQGTKVEIK
```

NI-203.26C11-PIMC-VK (variable light chain sequence VK) (SEQ ID NO: 6)

```
FR1--------------------CDR1----------FR2------------CDR2---FR3----
DIVMTQSPDSLAVSLGERATIKCKSSQSVLYSNKNFLAWYQQKPGQPPKLLIYWASTRESGVPDRFSGS

------------------------CDR3-----FR4-------
GSGTDFTLTISSLQAEDVAVYYCQQYYSNPNTFGQGTKLEIK
```

Fig. 1

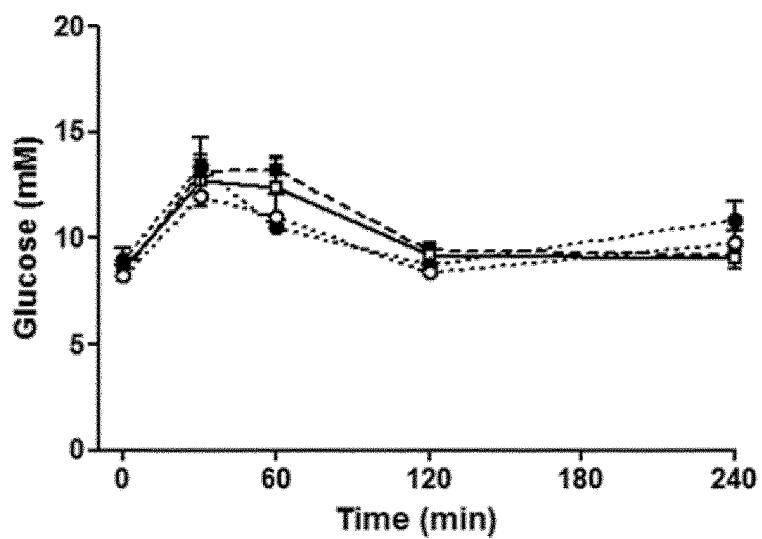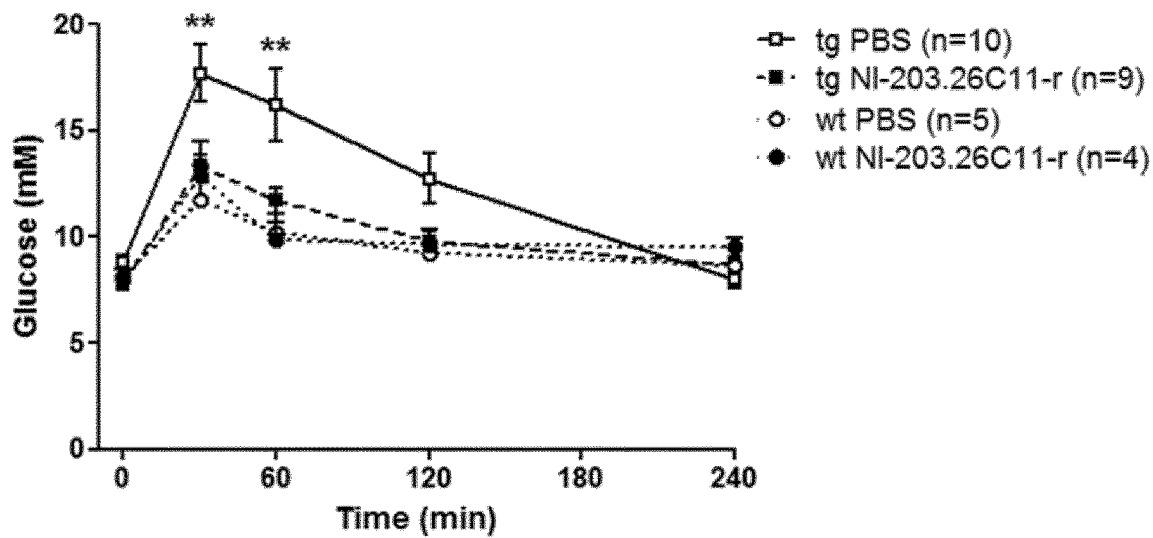
Fig. 10 it is regulated together with insulin, as increased insulin production leads to increased hIAPP levels. hIAPP is released from pancreatic β-cells into the blood circulation and is involved in glycemic regulation through gastric emptying and satiety control, in synergy with insulin.

COMPOUNDS CAPABLE OF ANTAGONIZING ISLET AMYLOID POLYPEPTIDE (IAPP) INDUCED BETA-CELL DAMAGE AND IMPAIRED GLUCOSE TOLERANCE

CROSS-REFERENCE TO RELATED APPLICATIONS

The present application is a U.S. national phase of International application no. PCT/EP2015/055238 (filed Mar. 12, 2015) which claims priority to EP14159194.1 (filed Mar. 12, 2014), the contents of each of which are incorporated by reference herein.

REFERENCE TO A SEQUENCE LISTING

This application contains a Sequence listing in computer readable form. The computer readable form is incorporated herein by reference.

FIELD OF THE INVENTION

The present invention generally relates to molecules specifically binding to human islet amyloid polypeptide (hIAPP) also known as amylin, particularly human antibodies as well as fragments, derivatives and variants thereof for antagonizing islet amyloid polypeptide (IAPP) induced β-cell damage and impaired glucose tolerance which are symptoms typically associated with diabetes mellitus type 2 (T2D).

BACKGROUND OF THE INVENTION

Protein accumulation, modifications and aggregation are pathological aspects of numerous metabolic diseases including well known neurodegenerative diseases such as Huntington's, Alzheimer's (AD) and Parkinson's diseases (PD) (Taylor et al., Science 296 (2005), 1991-1995). Pathological protein aggregation is also involved in metabolic diseases such as diabetes mellitus type 2 (T2D) and islet rejection following clinical pancreatic islet transplantation into individuals with diabetes mellitus type 1 (T1D). Misfolding and aggregation of proteins lead to the development of amyloid deposits and seem to be directly related to cell toxicity in these diseases. Islet amyloid polypeptide (IAPP or amylin), a physiological peptide co-secreted with insulin by β-cells in the pancreas, which forms fibrillar aggregates in pancreatic islets (also called islets of Langerhans) of T2D patients and has been suggested to play a role in the development of the disease (Westermark et al. (2011), Physiol. Rev. 91(3): 795-826). Furthermore, as mentioned before, IAPP aggregates have been found in pancreatic islets upon transplantation of isolated islets in patients with diabetes mellitus type 1 (T1D).

Human IAPP (hIAPP) is a peptide hormone that consists of 37 amino acids, with a disulfide bridge between cysteine residues 2 and 7 and an amidated C-terminus. Pancreatic islets are composed of 65 to 80% β-cells, which produce and secrete insulin and IAPP essential for regulation of blood glucose levels and cell metabolism. IAPP is processed from preprohormone preproIAPP, a 89 amino acid precursor produced in pancreatic β-cells.

PreproIAPP is rapidly cleaved after translation into proislet amyloid polypeptide, a 67 amino acid peptide, which undergoes additional proteolysis and post-translational modifications to generate hIAPP. hIAPP expression is regulated together with insulin, as increased insulin production leads to increased hIAPP levels. hIAPP is released from pancreatic β-cells into the blood circulation and is involved in glycemic regulation through gastric emptying and satiety control, in synergy with insulin.

In type-2 diabetes (T2D) genetic determinants and environmental factors lead to the development of insulin resistance followed by a compensatory increase in β-cell mass and insulin and amylin (hIAPP) secretion to maintain normal blood glucose levels. The resulting high concentrations of amylin favor the formation of toxic human islet amyloid polypeptide (hIAPP) oligomers and deposition of hIAPP fibrils which is found in more than 90% of T2D patients. The deposition of hIAPP correlates with the reduction in insulin producing β-cells and has also been proposed to play a role for the loss of β-cells in pancreatic islets transplanted into individuals with type-1 diabetes.

Type-2 diabetes is the most common form of diabetes, accounting for about 90% of all cases. The disease affects more than 200 million people worldwide resulting in more than a million deaths from diabetes annually. More than 300.000 patients are affected in Switzerland. The prevalence of diabetes is increasing dramatically in both developed and developing countries due to population growth, aging, urbanization, and increasing prevalence of obesity and physical inactivity. The global type-2 diabetes market at USD 25 billion is forecast to reach USD 35 billion by 2016 with a compound annual growth rate of 6.4% between 2009 and 2016. Current treatments include dietary management and pharmacological intervention acting on different pathways to decrease blood glucose levels by either improving insulin sensitivity or stimulating the pancreas to release insulin. None of the available treatments can however counteract the aggregation of hIAPP and the loss of pancreatic β-cells. New treatment strategies for type-2 diabetes involve analogues of glucagon-peptide 1 (GLP-1) and inhibitors of dipeptidyl-peptidase 4 (DPP 4), the enzyme which inactivates endogenous GLP-1. These strategies are based on the potent insulinotropic effect of GLP-1 and its effect to enhance beta-cell proliferation.

More recent and promising strategies involve the development of anti-inflammatory drugs or antibodies targeting the IL-1β pathway (Donath et al. (2008), Nat. Clin. Pract. Endocrinol. Metab. 4(5): 240-241; Ehes et al. (2009), Proc. Natl. Acad. Sci. USA 106(33): 13998-14003; Owyang et al. (2010), Endocrinology 151(6): 2515-2527; Dinarello et al. (2010), Curr. Opin. Endocrinol. Diabetes Obes. 17(4): 314-321; Boni-Schnetzler et al. (2011), J. Clin. Endocrinol. Metab. 93(10): 4065-4074; Boni-Schnetzler et al. (2012), Br. J. Clin. Pharmacol.; Cavelti-Weder et al. (2012), Diabetes Care). Of important note, recent studies show that hIAPP specifically induce the inflammasome—IL-1β system leading to activation of the innate immune system (Masters et al. (2010), Nat. Immunol. 11(10): 897-904; Mandrup-Poulsen et al. (2010), Nat. Immunol. 11(10): 881-883), thus supporting a therapeutic strategy targeting hIAPP aggregation.

Hitherto, active and passive immunotherapy approaches targeting hIAPP and/or proIAPP such as taught in international application WO03/092619 are based on and require the clearance of hIAPP fibrils and islet amyloid. However, so far no experimental evidence has been provided that immunotherapy could be successfully employed. To the contrary, in vivo studies showed that though vaccination was able to induce anti-toxic IAPP oligomer antibodies that do not prevent hIAPP-induced β-cell apoptosis in hIAPP transgenic mice; see Lin et al., Diabetes 56 (2007), 1324-1332.

Summarizing the above, novel therapeutic agents and strategies are urgently needed addressing hIAPP induced disorders such as β-cell damage, impaired glucose tolerance, abnormal weight gain, and the like.

SUMMARY OF THE INVENTION

The present invention generally relates to human islet amyloid polypeptide (hIAPP)-binding molecules for use in protecting β-cells from hIAPP induced cell damage and/or islet amyloid toxic effects; and/or restoring hIAPP induced impaired glucose tolerance in a subject in need thereof, preferably wherein the hIAPP-binding molecule selectively binds aggregated hIAPP in pancreas tissue of a human diabetic subject.

The present invention is inter alia based on the surprising observation that the level binding of a hIAPP-binding molecule such as anti-IAPP antibody to IAPP aggregates formed in vitro and to in vivo IAPP aggregates in pancreatic tissue obtained from diabetic patients is not predictive with respect to in vivo activity and thus therapeutic utility. Thus, preselection of candidate compounds based on in vitro assays may sort out biologically active agents at first place because of their inferior performance in vitro. Hence, since animal testing is laborious and time consuming biochemical and cell-based in vitro assays are first choice to select drug candidate. This is particular true for transgenic IAPP animal models for diabetes since for example mouse models hitherto available either do not spontaneously develop diabetes or only spontaneously develop diabetes with hyperglycemia and impaired glucose tolerance by 6 to 10 months of age. In addition, often only minimal amyloid deposition is observed in mice spontaneously developing diabetes or only 12 to 24 months of age.

Thanks to the present invention, a novel IAPP transgenic animal model is provided, see Examples, useful as a reliable screening system of candidate compounds, making testing possible in a reasonable time and thus amenable on an industrial and pharmaceutical scale, respectively. In particular, the animal model of the present invention spontaneously develops diabetes characterized by impaired glucose tolerance and hyperglycemia already present at 1-month and 2-month of age (FIG. 4), respectively, and extracellular amyloid deposits appear at 2-month of age and extensive amyloidosis is observed at 4-month of age, with associated β-cell loss. Thus, due to the relative short time of development of pathophysiology in the transgenic animal of the present invention including the clinical relevant medical indications observed in human subjects suffering from diabetes, the new animal model is particularly suited for the screening and validation of anti-diabetic agents. Of course, though the animal model of the present invention is particularly suited for assaying IAPP-binding molecules, also other candidate compounds can be tested, for example agents which act down- or upstream the IAPP/insulin targeted pathway and/or are capable of antagonizing or ameliorating the medical indications induced by the heterologous expression of IAPP in the animal.

As demonstrated in Examples, in accordance with the present invention a hIAPP-binding molecule selectively binding aggregated hIAPP in pancreas tissue of a human diabetic subject (FIGS. 2 and 3) could be proved to be effective in protecting β-cells from hIAPP induced cell damage and islet amyloid toxic effects (FIG. 7), restoring hIAPP induced impaired glucose tolerance (FIG. 8), increasing insulin secretion (FIG. 7), decreasing fasting glucose (FIG. 8) and normalizing body weight gain (FIG. 8). Thus, a hIAPP-binding molecule of the present invention is particularly useful in the treatment of a subject suffering from or is at risk of developing diabetes mellitus type 2 (T2D) and/or hypertension which are commonly associated with one or more of the above-mentioned medical indications.

In this context, preliminary results from experiments performed in accordance with the present invention suggest that β-cell protection is achieved independently of islet amyloid deposit removal. Thus, the IAPP antagonizing effect of the hIAPP-binding molecule of the present invention may indeed not be due to clearance of IAPP fibrils and/or prevention of IAPP fibril formation thought in the prior art to be necessary for therapeutic utility of an IAPP-specific anti-diabetic agent. These observations compare with those reported for exendin-4, approved as a medicament (Exenatide; BYETTA®) for the treatment of diabetes type 2 in that exendin-4 increases islet amyloid deposition but offsets the resultant β-cell toxicity in human islet amyloid polypeptide transgenic mouse islets; see Aston-Mourney et al., Diabetologia 54 (2011), 1756-1765). Accordingly, in one embodiment of the present invention, β-cell protection mediated by the hIAPP-binding molecule is unrelated with islet amyloidosis in the subject.

In further experiments performed in accordance with the present invention, it could be shown that a hIAPP binding molecule of the present invention, i.e. the subject antibody NI-203.26C11 is capable of binding aggregated structures in early phases of their development; see Example 5. In particular, subject antibody NI-203.26C11 binds to initial structures which merely show fibrillary characteristics, i.e. proteins which assemble to form insoluble fibers, but are not of fibrillary morphology, yet can be detected with the hIAPP binding molecule of the present invention; see FIG. 9. Accordingly, in one embodiment the hIAPP binding molecule of the present invention is capable of and used for, respectively, in early detection of fibrillary IAPP structures. In a preferred embodiment, the IAPP binding molecule detects hIAPP aggregates when first assembling of hIAPP take place.

In view of the property of the subject antibody to bind early fibrillary structures, in one embodiment the hIAPP binding molecule of the present invention is used in the treatment, protection and/or amelioration of hIAPP induced cell damage, islet amyloid toxic effects, and/or restoring hIAPP induced impaired glucose tolerance in early phases of fibrillar development. Therefore, the hIAPP-binding molecule in accordance with the present invention preferably selectively binds early fibrillary aggregated hIAPP in pancreas tissue of a human diabetic subject.

An impaired glucose tolerance, whereas fasting glycemia is in reference range, the post-prandial phase is characterized by a rapid and large increase in blood glucose levels. This abnormally high glucose (blood sugar) level is a characteristic for hyperglycemia, a hallmark sign of diabetes. As demonstrated in Example 6 and 7 and shown in FIGS. 8 and 10, the administration of the subject anti-hIAPP antibody to the IAPP transgenic animals normalizes the blood glucose level and thus could be useful in the prevention or treatment of hyperglycemia. Therefore, in one embodiment of the present invention the hIAPP-binding molecule is used in normalizing blood glucose level. Furthermore, as also demonstrated in Example 6 and shown in FIG. 8 the administration of the subject anti-hIAPP antibody let to a normalization of the body weight gain associated with hIAPP in the animal model. Therefore, in one embodiment, the hIAPP-binding molecule is used for normalizing body weight, typically associated with hIAPP.

In principle any hIAPP-binding and interacting molecule, respectively, which selectively binds aggregated hIAPP in pancreas tissue of a human diabetic subject may be used in accordance with the present invention. The term hIAPP-binding molecule in accordance with the present invention is also meant to encompass any precursor and individual components of the molecule. For example, if the hIAPP-binding molecule referred to is a peptide, polypeptide or protein such as an antibody, IAPP derivative or peptide inhibitor the respective term also includes the polynucleotide encoding such molecule, the vector, in particular expression vector comprising the coding sequence of the molecule as well as the host cell comprising the polynucleotide or vector. Diabetic pancreatic tissue specific hIAPP binding of a candidate compound can be determined as shown in FIGS. 2 and 3 and in accordance with Example 1 and validation of the candidate compound can performed with the new animal model of the present invention as illustrated in Examples 1 and 3. However, in case of small organic molecules determination of their interaction with hIAPP on/in pancreatic tissue may be cumbersome. Instead, the person skilled in the art may rely on biochemical binding assays and affinity labelling techniques known in the art; see, e.g., Lomenick et al., Identification of direct protein targets of small molecules in ACS Chem. Biol. (2011), 34-46 and Jiang et al., Structure-based discovery of fiber-binding compounds that reduce the cytotoxicity of amyloid beta in eLife 2013; 2:e00857; published online. Positive hits may then directly applied the compound to the animal model of the present invention for validation.

A "binding molecule" as used in the context of the present invention relates primarily to antibodies, and fragments thereof, but may also refer to other non-antibody molecules that selectively and dose-dependently recognize pathological hIAPP aggregates in the pancreas of patients diagnosed with diabetes mellitus type 2 (T2D) and exhibit the functional properties of the NI-203.26C11 antibody illustrated in the Examples including but not limited to hormones, receptors, ligands, major histocompatibility complex (MHC) molecules, chaperones such as heat shock proteins (HSPs) as well as cell-cell adhesion molecules such as members of the cadherin, intergrin, C-type lectin, immunoglobulin (Ig) superfamilies and in particular designed ankyrin repeat proteins (DARPins) which are a promising class of non-immunoglobulin proteins that can offer advantages over antibodies for target binding; see for review, e.g., Stumpp and Amstutz, Curr. Opin. Drug Discov. Devel. 10 (2007), 153-159, and references cited therein. Thus, for the sake of clarity only and without restricting the scope of the present invention most of the following embodiments are discussed with respect to antibodies and antibody-like molecules which represent the preferred binding molecules for the development of therapeutic agents. Antibodies or antigen-binding fragments, immunospecific fragments, variants, or derivatives thereof of the invention include, but are not limited to, polyclonal, monoclonal, multispecific, murine, human, humanized, primatized, murinized or chimeric antibodies, a recombinant full antibody (immunoglobulin), in particular a monoclonal recombinant full antibody (immunoglobulin), single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to antibodies disclosed herein), a chimeric antibody, a CDR-grafted antibody, a bivalent antibody-construct, a synthetic antibody, a cross-cloned antibody, a fully-human antibody, a humanized antibody, a xenogenic or a chimeric human-murine antibody, nanobodies, diabodies, and the like. ScFv molecules are known in the art and are described, e.g., in U.S. Pat. No. 5,892,019 Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In a preferred embodiment of the present invention the hIAPP-binding molecule is immunologically active in that it is amenable to histochemical staining, thereby allowing easy identification of binding to pancreatic tissue obtained from patients, which contains IAPP aggregates. Accordingly, in a particularly preferred embodiment of the present invention the hIAPP-binding molecule is an anti-hIAPP antibody or hIAPP-binding fragment thereof. Most preferably the antibody is a human-derived antibody. hIAPP-binding molecules of the present invention may be identified and characterized in vitro, cloned and produced recombinantly by Neurimmune's RTM™ technology as described in detail in international application WO2008/081008. In addition, or alternatively the screening process for presence and affinity of hIAPP binding molecules may comprise the steps of a sensitive tissue amyloid plaque immunoreactivity (TAPIR) assay such as described in international application WO2004/095031, the disclosure content of which is incorporated herein by reference, performed here in analogy for amyloid deposits on pancreatic islets.

Preferably, the human anti-hIAPP antibodies for use in accordance with the present invention have been isolated from a pool of healthy human subjects or from pools of obese patients and other patients groups with enhanced risk to develop T2D, which at the time of antibody isolation preferably showed no signs of T2D, but amyloid deposition and exhibit an IAPP specific immune response. The so human-derived antibodies may also be called "human autoantibodies" in order to emphasize that those antibodies were indeed expressed initially by the subjects and are not in vitro selected constructs generated, for example, by means of human immunoglobulin expressing phage libraries or xenogeneic antibodies generated in a transgenic animal expressing part of the human immunoglobulin repertoire, which hitherto represented the most common method for trying to provide human-like antibodies. On the other hand, the human-derived antibody of the present invention may be denoted synthetic, recombinant, and/or biotechnological in order distinguish it from human serum antibodies per se, which may be purified via protein A or affinity column.

In a preferred embodiment of the present invention, the hIAPP-binding molecule is derived from a human-derived monoclonal anti-hIAPP antibody disclosed in applicant's co-pending international application WO2014/041069, the disclosure content of which is incorporated herein by reference, in particular with respect to the amino acid sequences of the anti-hIAPP antibodies, their CDRs and variable region, the recombinant production of the anti-hIAPP antibodies as well as the Examples describing assays useful for testing the immunological and biological activity of the anti-hIAPP antibodies and equivalent antibodies. In addition, unless otherwise stated, a term as used herein such as "IAPP" and "CDR" herein is given the definition as provided in international application WO2014/041069, supra.

As shown in the accompanying Examples, the present invention is illustrated with a human-derived anti-hIAPP antibody NI-203.26C11. The binding specificity of an antibody is mostly determined by its binding domain comprising a variable heavy and light chain region, and in particular by one or more the complementarity determining regions (CDRs) contained therein. As known in the art, mutations in the framework region and/or in the CDRs may not substantially affect binding specificity but could even enhance affinity. For example, the person skilled in the art knows that binding affinity may be enhanced by making amino acid substitutions within the CDRs or within the hypervariable loops (Chothia and Lesk, J. Mol. Biol. 196 (1987), 901-917) which partially overlap with the CDRs as defined by Kabat; see, e.g., Riechmann, et al, Nature 332 (1988), 323-327. Thus, the present invention also relates to antibodies wherein one or more of the CDRs of the original antibody comprise one or more, preferably not more than two amino acid substitutions.

Therefore, in one embodiment any one of the above-described hIAPP-binding molecules of the present invention comprises in its binding domain
(a) at least one complementarity determining region (CDR) of the heavy chain (VH) and/or a light variable (VL) region amino acid sequence depicted in FIG. 1 (SEQ ID NOs: 2, 4, and 6);
(b) an amino acid sequence of the VH and/or VL region as depicted in FIG. 1;
(c) at least one CDR consisting of an amino acid sequence resulted from a partial alteration of any one of the amino acid sequences of (a); and/or
(d) a heavy chain and/or a light variable region comprising an amino acid sequence resulted from a partial alteration of any one of the amino acid sequences of (b).

Antibody NI-203.26C11 is one of the anti-IAPP antibody disclosed in the above-mentioned international application WO2014/041069. Pepscan analysis of IAPP binding epitopes of the human recombinant antibodies described therein revealed a sequence within the human IAPP including aa 2-CNTATCA-8 (SEQ ID NO: 7) as the unique linear epitope recognized by antibody NI-203.26C11. Recent experimental data on epitope fine mapping of antibody NI-203.26C11 revealed that NI-203.26C11 binds hIAPP at the N-terminus, with a critical role for the amino acids 2, 3, 4, and 7. In particular, the presence of the amino acids 2 and 7 seems to be necessary for binding since for example lack or mutation of the amino acid position 2 substantially abolishes IAPP binding of antibody NI-203.26C11. Accordingly, in order to determine anti-IAPP antibodies which are equivalent to the antibody NI-203.26C11 besides common completion assays antigen binding assays may be used, in particular ELISA for determining whether a given anti-IAPP antibody displays substantially the binding preference, i.e. 2-CNTATCA-8 (SEQ ID NO: 7) with the mentioned mandatory amino acid positions.

Preferably, the hIAPP-binding molecule of the invention comprises in one or both of its immunoglobulin chains two or all three CDRs of the variable regions as set forth in FIG. 1.

In a preferred embodiment of the present invention, the hIAPP-binding molecule such as anti-hIAPP antibody is encoded by a polynucleotide which comprises, consists essentially of, or consists of a nucleic acid having a polynucleotide sequence of the $V_H$ or $V_L$ region of an anti-IAPP antibody as depicted in Table I. In this respect, the person skilled in the art will readily appreciate that the polynucleotides encoding at least the variable domain of the light and/or heavy chain may encode the variable domain of both immunoglobulin chains or only one. In one embodiment therefore, the polynucleotide comprises, consists essentially of, or consists of a nucleic acid having a polynucleotide sequence of the $V_H$ and the $V_L$ region of an anti-IAPP antibody as depicted in Table I.

TABLE I

Nucleotide sequences of the $V_H$ and $V_L$ region of anti-hIAPP antibody.

| Antibody | Nucleotide sequences of variable heavy (VH) and variable light (VL/VK) chains |
|---|---|
| NI-203.26C11-$V_H$ | CAGGTGCAGCTGCAGGAGTCGGGCCCAGGATTGGTGAAGCCTTCTC<br>AGACCCTGTCCCTCACCTGCACTGTCTCTGGTGGCTCCATCAGCAGT<br>GGTAATTACTACTGGACCTGGATCCGGCAGCCCGCCGGGAAGGGA<br>CTGGAGTGGATTGGGCATATCTATTCCAGTGGGACCACCAATTACA<br>ACCCCTCCCTCGAGAGTCGAGTCACCATTTCAGTAGACACGTCCAA<br>GAACCAGTTCTCCCTGAGCCTGAACTCTGTGACCGCCGCAGACACG<br>GCCGTTTATTACTGTGCGAGACCACTGGCTACAGTTCCGGATGCTTT<br>TAATATCTGGGGCCAAGGGACAATGGTCACCGTCTCTTCG<br>SEQ ID NO: 1 |
| NI-203.26C11-$V_K$ | GAAATTGTGATGACTCAGTCTCCAGACTCCCTGGCTGTGTCTCTGGG<br>CGAGAGGGCCACCATCAAGTGCAAGTCCAGCCAGAGTGTTTTATAC<br>AGCAATAAGAACTTCTTAGCTTGGTACCAGCAGAAACCAGGACAGC<br>CTCCTAAATTACTCATTTACTGGGCATCTACTCGGGAATCCGGGGTC<br>CCTGACCGATTCAGTGGCAGCGGGTCTGGGACAGATTTCACTCTCA<br>CCATCAGCAGCCTGCAGGCTGAAGATGTGGCAGTTTATTACTGTCA<br>GCAGTATTATAGTAATCCTAACACTTTTGGCCAGGGGACCAAGGTG<br>GAGATCAAA<br>SEQ ID NO: 3 |
| NI-203.26C11-PIMC $V_K$ | GATATTGTGATGACTCAATCACCAGACTCCCTGGCTGTGTCTCTGGG<br>CGAGAGGGCCACCATCAAGTGCAAGTCCAGCCAGAGTGTTTTATAC<br>AGCAATAAGAACTTCTTAGCTTGGTACCAGCAGAAACCAGGACAGC<br>CTCCTAAATTACTCATTTACTGGGCATCTACTCGGGAATCCGGGGTC<br>CCTGACCGATTCAGTGGCAGCGGGTCTGGGACAGATTTCACTCTCA<br>CCATCAGCAGCCTGCAGGCTGAAGATGTGGCAGTTTATTACTGTCA<br>GCAGTATTATAGTAATCCTAACACTTTTGGCCAGGGGACCAAGCTG<br>GAGATCAAG<br>SEQ ID NO: 5 |

Alternatively, the hIAPP-binding molecule for use in accordance with the present invention competes for binding to the hIAPP aggregates in pancreatic tissue with the antibody having the VH and VL region as depicted in FIG. 1. Those hIAPP-binding molecules may be antibodies, for example murine, humanized, xenogeneic, chimeric human-murine or preferably human derived-antibodies, in particular for therapeutic applications. However, for diagnostic uses and research in general murine antibodies are suitable as well. An antigen-binding fragment of the antibody can be, for example, a single chain Fv fragment (scFv), a F(ab') fragment, a F(ab) fragment, and an F(ab')2 fragment. For some applications only the variable regions of the antibodies are required, which can be obtained by treating the antibody with suitable reagents so as to generate Fab', Fab, or F(ab")$_2$ portions. Such fragments are sufficient for use, for example, in immunodiagnostic procedures involving coupling the immunospecific portions of immunoglobulins to detecting reagents such as radioisotopes.

The exemplary IAPP-binding molecule, i.e. anti-hIAPP antibody could also be shown to not recognize pathological Aβ deposits in a human brain with Alzheimer's disease. Therefore, in one embodiment the hIAPP-binding molecule of the present invention does not recognize pathological Aβ deposits in a human brain with Alzheimer's disease.

In one embodiment of the present invention, the hIAPP-binding molecule comprises a polypeptide sequence which is heterologous to the hIAPP-binding domain, e.g. VH and/or VL region and/or to the at least one CDR. Heterologous polypeptide sequences include but are not limited to binding domains of different specificity, peptide linkers, peptide tags, N- and C-terminal peptide moieties, Fc domains, and the like, either alone or in combination. Of course, in addition or alternatively the IAPP-binding molecule of the present invention may contain non-peptide moieties such as polyethylene glycol, which may be added via chemical or biochemical means and methods in vitro.

The hIAPP-binding molecule for use in accordance with the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook et al., Molecular Cloning A Laboratory Manual, Cold Spring Harbor Laboratory N.Y. (1989) and Ausubel, Current Protocols in Molecular Biology, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment or removal of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO 00/30680 for corresponding technical details.

In a preferred embodiment, the hIAPP-binding molecule of the present invention comprises a constant domain or part thereof which is heterologous to the binding domain, e.g. VH and/or VL region and/or to the at least one CDR, preferably wherein the constant domain is a human constant domain. Preferably, the constant domain is of the IgG type, preferably of the IgG1 class or isotype; see, e.g., Kipriyanov and Le Gall, Molecular Biotechnology 26 (2004), 39-60; Chan and Carter, Nature Reviews Immunology 10 (2010), 301-316; Vincent and Zurini, Biotechnol J. 7 (2012), 1444-1450.

Hence, the present invention relates to any hIAPP-binding molecule as described and defined hereinabove having the functional and biological features which make the molecule useful in protecting β-cells from hIAPP induced cell damage and/or islet amyloid toxic effects; and/or restoring hIAPP induced impaired glucose tolerance in a subject in need thereof.

In a further embodiment of the present invention, the hIAPP-binding molecule for use in accordance with the present invention is detectably labeled or otherwise linked to a functional moiety. Labeling agents can be coupled either directly or indirectly to the hIAPP-binding molecule of the invention. One example of indirect coupling is by use of a spacer moiety. Furthermore, the hIAPP-binding molecule of the present invention can comprise a further domain, said domain being linked by covalent or non-covalent bonds. The linkage can be based on genetic fusion according to the methods known in the art and described above or can be performed by, e.g., chemical cross-linking as described in, e.g., international application WO 94/04686. The additional domain present in the fusion protein comprising the hIAPP-binding molecule of the invention may preferably be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the hIAPP-binding molecule of the invention or vice versa. The therapeutically or diagnostically active agent can be coupled to the hIAPP-binding molecule of the invention by various means. This includes, for example, single-chain fusion proteins comprising the variable regions of an anti-hIAPP antibody of the invention coupled by covalent methods, such as peptide linkages, to the therapeutically or diagnostically active agent. Further examples include molecules which comprise at least an antigen-binding fragment coupled to additional molecules covalently or non-covalently include those in the following non-limiting illustrative list. Traunecker, Int. J. Cancer Surp. SuDP 7 (1992), 51-52, describe the bispecific reagent janusin in which the Fv region directed to CD3 is coupled to soluble CD4 or to other ligands such as OVCA and IL-7. Similarly, the variable regions of the antibody of the invention can be constructed into Fv molecules and coupled to alternative ligands such as those illustrated in the cited article. Higgins, J. Infect. Dis. 166 (1992), 198-202, described a hetero-conjugate antibody composed of OKT3 cross-linked to an antibody directed to a specific sequence in the V3 region of GP120. Such hetero-conjugate antibodies can also be constructed using at least the variable regions contained in the anti-hIAPP antibody of the invention methods. Additional examples of specific antibodies include those described by Fanger, Cancer Treat. Res. 68 (1993), 181-194 and by Fanger, Crit. Rev. Immunol. 12 (1992), 101-124. Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

The above described fusion protein may further comprise a cleavable linker or cleavage site for proteinases. These spacer moieties, in turn, can be either insoluble or soluble (Diener et al., Science 231 (1986), 148) and can be selected to enable drug release from the anti-hIAPP antibody at the target site. Examples of therapeutic agents which can be coupled to the antibodies of the present invention for immunotherapy are drugs, radioisotopes, lectins, and toxins. The drugs with which can be conjugated to the antibodies and antigens of the present invention include compounds which are classically referred to as drugs such as mitomycin C, daunorubicin, and vinblastine. In using radioisotopically conjugated antibodies or antigens of the invention for, e g immunotherapy, certain isotopes may be more preferable than others depending on such factors as leukocyte distribution as well as stability and emission. Depending on the autoimmune response, some emitters may be preferable to others. In general, α and β particle emitting radioisotopes are preferred in immunotherapy. Preferred emitters are short range, high energy emitters such as $^{212}$Bi. Examples of radioisotopes which can be bound to the antibodies or antigens of the invention for therapeutic purposes are $^{125}$I, $^{131}$I, $^{90}$Y, $^{67}$Cu, $^{212}$Bi, $^{212}$At, $^{211}$Pb, $^{47}$Sc, $^{109}$Pd and $^{188}$Re. Most preferably, the radiolabel is $^{64}$Cu. Other therapeutic agents which can be coupled to the antibody or antigen of the invention, as well as ex vivo and in vivo therapeutic protocols, are known, or can be easily ascertained, by those of ordinary skill in the art. Wherever appropriate the person skilled in the art may use a polynucleotide encoding the hIAPP-binding molecule of the invention instead of the proteineous material itself.

In one embodiment, the hIAPP-binding molecule disclosed herein is (a) detectably labeled, preferably wherein the detectable label is selected from the group consisting of an enzyme, a radioisotope, a fluorophore, nuclear magnetic and a heavy metal; or (b) attached to a drug.

For pharmaceutical use, the hIAPP-binding molecule in accordance with the present invention is formulated in a pharmaceutical composition; optionally further comprising a pharmaceutically acceptable carrier. Preferably, the hIAPP-binding molecule is designed to be administered subcutaneously (s.c.), intramuscularly (i.m.), or intravenously (i.v.); and/or on a weekly, biweekly or monthly basis. In one embodiment, the hIAPP-binding molecule is designed to be administered before or after onset of islet amyloid fibrils, protofibrils and/or amyloid plaque in pancreatic tissue. As could be shown Example 2 and FIG. 4, impaired glucose tolerance precedes the deposition of islet amyloids in the transgenic mouse model of type-2 diabetes (hIAPP transgenic mice). Therefore, a subject suffering from impaired glucose tolerance and/or showing aberrant expression of IAPP compared to a healthy subject may already be treated in the absence of IAPP amyloid plaque or fibril formation in pancreatic islet, thereby preventing the onset of more deleterious medical indications of diabetes.

In one embodiment of the hIAPP-binding molecule of the present invention, the pharmaceutical composition further comprises an agent capable of preventing or reducing IAPP amyloid formation, preferably wherein said agent is selected from the group of consisting of flavonoids, IAPP analogues, metformin, and thiazolidinediones such as rosiglitazone; see, e.g., Cao and Raleigh, Biochemistry 51 (2012), 2670-2683; Noor et al., Protein Sci. 21 (2012), 373-382; Yan et al., PNAS 103 (2006), 2046-2051; and Hull et al., Diabetes 54 (2005), 2235-2244. Alternatively, the hIAPP-binding molecule of the present invention may be designed to be co-administered, i.e. concomitantly before, in conjunction or after administration of such agent to the subject. For example, a diabetic patient may already receive a treatment with an anti-diabetic drug, which however proved not to be successful and/or sufficient to remedy all of the medical indications and symptoms, respectively. In this case, the prior treatment may be supplement with administration of the hIAPP-binding molecule in accordance with the present invention. A combination therapy is particularly preferred during the progress of diseases. In the context of the present application, "co-administration" of two or more compounds is defined as administration of the two or more compounds to the patient within 24 h, including separate administration of two medicaments each containing one of the compounds as well as simultaneous administration whether or not the two compounds are combined in one formulation or whether they are in two separate formulations. A "synergistic effect" of two compounds is in terms of statistical analysis an effect which is greater than the additive effect which results from the sum of the effects of the two individual compounds.

Whether or not a given hIAPP-binding molecule for use in accordance with the present invention may be therapeutically effective can be determined by using the animal model of the present invention and disclosed in the appended Examples. Preferably, the hIAPP-binding molecule is effective when administered at a dosage of about 10 mg/kg in a transgenic hIAPP mouse model and/or about 3 mg/kg in a transgenic hIAPP rat model in relation an anti-hIAPP IgG antibody. Accordingly, in case of using hIAPP-binding fragments such as single chain antibodies or using small organic molecules the dosage may be adjusted in relation to the molecular weight of an antibody.

A typical dose can be, for example, in the range of 0.001 to 1000 µg (or of nucleic acid for expression or for inhibition of expression in this range); however, doses below or above this exemplary range are envisioned, especially considering the aforementioned factors. Generally, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The term "subject" and "patient" is used interchangeably herein and means an individual in need of a treatment of a metabolic disease. Preferably, the subject is a mammal, particularly preferred a human.

"Treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. As used herein, the terms "treat" or "treatment" refer to both therapeutic treatment and prophylactic or preventative measures, wherein the object is to prevent or slow down (lessen) an undesired physiological change or disorder, such as the development or spread of a metabolic disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

For use as a pharmaceutical composition, the hIAPP-binding molecule according to the invention, optionally combined with other active agents, may be incorporated together with one or more inert conventional carriers and/or diluents. Pharmaceutically acceptable carriers and administration routes can be taken from corresponding literature known to the person skilled in the art. The pharmaceutical compositions of the present invention can be formulated according to methods well known in the art; see for example Remington: The Science and Practice of Pharmacy (2000) by the University of Sciences in Philadelphia, ISBN 0-683-306472, Vaccine Protocols, 2nd Edition by Robinson et al., Humana Press, Totowa, N.J., USA, 2003; Banga, Therapeutic Peptides and Proteins: Formulation, Processing, and Delivery Systems. 2nd Edition by Taylor and Francis. (2006), ISBN: 0-8493-1630-8. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods. Pharmaceutical compositions for oral administration, such as single domain antibody molecules (e.g., "Nanobodies™") etc. are also envisaged in the present invention.

Such oral formulations may be in tablet, capsule, powder, liquid or semi-solid form. A tablet may comprise a solid carrier, such as gelatin or an adjuvant. Further guidance regarding formulations that are suitable for various types of administration can be found in Remington's Pharmaceutical Sciences, Mace Publishing Company, Philadelphia, Pa., 17th ed. (1985) and corresponding updates. For a brief review of methods for drug delivery see Langer, Science 249 (1990), 1527-1533. In one embodiment, the hIAPP-binding molecule and composition of the invention is administered to a human patient once daily, each other day, thrice weekly, twice weekly or once weekly, preferably less than once daily.

As mentioned above, in a further aspect the present invention relates to a transgenic non-human animal for use in determining whether a test compound is capable of protecting β-cells from hIAPP induced cell damage and/or islet amyloid toxic effects; and/or restoring hIAPP induced impaired glucose tolerance; wherein the animal is characterized by being capable of expressing at least one transgene comprising a DNA sequence encoding a human islet amyloid polypeptide (hIAPP), and (i) spontaneously developing diabetes characterized by impaired glucose tolerance and/or hyperglycemia at about 1-month and 2-month of age, respectively; and/or (ii) appearance of extracellular amyloid deposits at about 2-month of age and/or extensive amyloidosis associated β-cell loss at about 4-month of age; see Example 4 and FIG. 4.

Preferably, the test compound is a hIAPP-binding molecule as defined hereinbefore.

As described in the Example the DNA sequence encoding hIAPP is preferably operably linked to the rat insulin II promoter. Furthermore, the transgenic animal of the present invention is preferably hemizygous; see, e.g., Cho et al., Curr Protoc Cell Biol. (2009), Chapter: unit-19.11; Haruyama et al., Curr Protoc Cell Biol. (2009), Chapter: unit-19.11.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

Several documents are cited throughout the text of this specification. The contents of all cited references (including literature references, issued patents, published patent applications as cited throughout this application and manufacturers specifications, instructions, etc.) are hereby expressly incorporated by reference; however, there is no admission that any document cited is indeed prior art as to the present invention.

A more complete understanding can be obtained by reference to the following specific Examples and Figures which are provided herein for purposes of illustration only and are not intended to limit the scope of the invention.

DESCRIPTION OF THE DRAWINGS

FIG. 1: Amino acid sequences of the variable region, i.e. heavy chain (SEQ ID NO: 2) and kappa light chain (SEQ ID NO: 4) of human IAPP antibody NI-203.26C11 and kappa light chain (SEQ ID NO: 6) of human IAPP antibody NI-203.26C11-PIMC-VK. Framework (FR) and complementarity determining regions (CDRs) are indicated with the CDRs being underlined. The heavy chain joining region (JH) and light chain joining region (JK) are indicated as well. Due to the cloning strategy the amino acid sequence at the N-terminus of the heavy chain and light chain may potentially contain primer-induced alterations in FR1, which however do not substantially affect the biological activity of the antibody. In order to provide a consensus human antibody, the nucleotide and amino acid sequences of the original clone were aligned with and tuned in accordance with the pertinent human germ line variable region sequences in the database; see, e.g., Vbase (http://vbase.mrc-cpe.cam.ac.uk/) hosted by the MRC Centre for Protein Engineering (Cambridge, UK). The amino acid sequence of human antibodies is indicated when N-terminus amino acids are considered to potentially deviate from the consensus germ line sequence due to the PCR primer and thus have been replaced by primer-induced mutation correction (PIMC).

FIG. 10: NI-203.26C11 antibody normalizes glucose tolerance in a transgenic rat model of type-2 diabetes (hIAPP transgenic rats). Recombinant rat chimeric NI-203.26C11 antibody was administered once-weekly to hIAPP transgenic rats (tg NI-203.26C11-r, n=9; 3 mg/kg i.p.) and wild-type rats (wt NI-203.26C11-r, n=4; 3 mg/kg i.p.). PBS was used as vehicle in hIAPP transgenic rats (tg PBS, n=10) and wild-type rats (wt PBS, n=5). (A) Oral glucose tolerance test (oGTT) before treatment in 3 month-old hIAPP transgenic rats and wild-type rats showing equivalent blood glucose levels. (B) NI-203.26C11-r antibody normalizes blood glucose levels in hIAPP transgenic rats during an oGTT performed after 8 weeks of treatment, as compared with tg PBS and wt PBS rats. NI-203.26C11-r antibody does not affect blood glucose levels in wild-type rats (wt NI-203.26C11-r). tg NI-203.26C11-r compared with tg PBS: ** $p<0.01$.

EXAMPLES

Methods

Antibody

Figure 2:
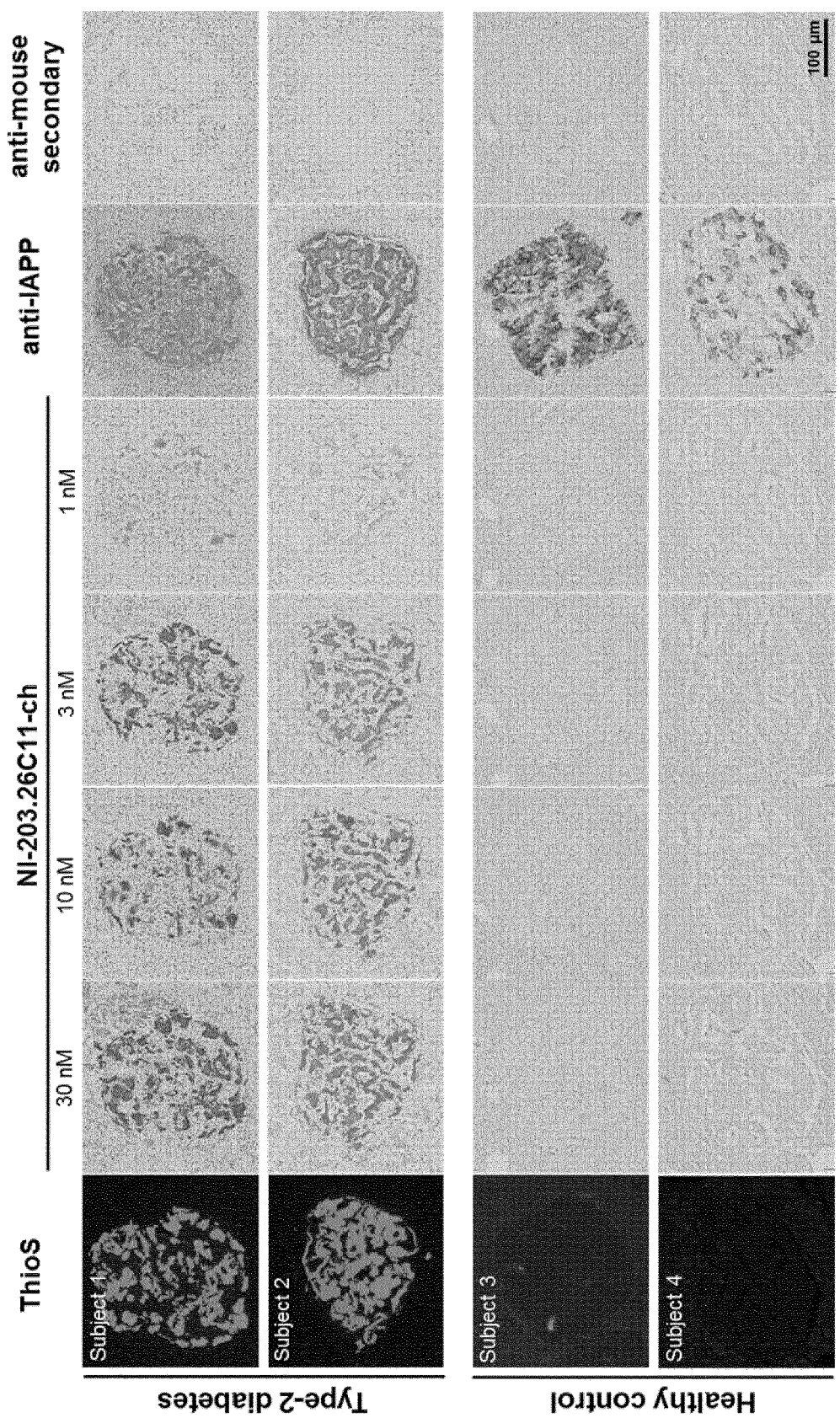
FIG. 2: NI-203.26C11 antibody selectively and dose-dependently recognizes pathological hIAPP aggregates in the pancreas of patients diagnosed with diabetes mellitus type 2 (T2D). Thioflavin S (ThioS, left panels, green) staining of islet amyloid in pancreatic islets of T2D patients but not in healthy controls. NI-203.26C11 antibody shows a staining in T2D pancreatic islets loaded with islet amyloids (Subjects 1 and 2) but not in healthy control pancreatic islets lacking islet amyloids (Subjects 3 and 4). Detection of hIAPP aggregates on amyloid positive T2D pancreatic islets with recombinant mouse chimeric antibody NI-203.26C11 (NI-203.26C11-ch; brown) at 3, 10, 30 nM (strong staining), and 1 nM (weak staining). NI-203.26C11 antibody does not recognize physiological hIAPP on healthy control pancreases. Anti-IAPP antibody (1:100; anti-IAPP) and secondary donkey anti-mouse antibody only (anti-mouse secondary) were used as positive and negative controls, respectively. Counterstaining was performed to visualize cell nuclei (faint blue i.o., faint staining here). Scale bar: 100 µm.

Human-derived antibodies targeting aggregated species of human IAPP (hIAPP) were identified by high-throughput analyses of full complements of the human memory B-cell repertoire derived from clinically selected populations of aged human subjects. Antibody cDNAs derived from hIAPP-reactive memory B-cells were expressed for the determination of binding properties. To avoid neutralizing mouse and rat anti-human antibody responses directed against human IgG, chimeric antibodies consisting of human variable domains and mouse or rat constant regions were generated by protein engineering. hIAPP-reactive IgG clones were recombinantly produced in CHO for in vitro characterization and in vivo validation studies in transgenic mice and rats. Protein expression was scaled up to 20 liter wave reactors to allow for production of antibodies at 100 mg scale. Antibodies were purified endotoxin-free by affinity chromatography.

Mice

Mice were obtained from The Jackson Laboratory (Bar Harbor, Me.). Hemizygous transgenic male mice (F1) with islet β-cell expression of hIAPP driven by the rat insulin II promoter and wild-type male mice (F1) on a FVB/NxDBA/2J background were generated by breeding hIAPP transgenic FVB/N (FVB/N-Tg(Ins2-IAPP)RHFSoel/J) males with DBA/2J wild-type female mice. Transgenic status was determined by PCR of genomic DNA using oligonucleotide primers directed against the hIAPP transgene.

The mice showed an early onset of the metabolic phenotype, i.e. the mice spontaneously developed diabetes characterized by impaired glucose tolerance and hyperglycemia already present at 1-month and 2-month of age, respectively. Mouse models previously described did not spontaneously develop diabetes and spontaneously develop diabetes with hyperglycemia and impaired glucose tolerance by 6 to 10 months of age, see e.g. Couce et al. Diabetes 45 (1996), 1094-1101); Soeller et al. Diabetes 47 (1998), 743-750; Hull et al. Diabetes 52(2) (2003), 372-379; Hull et al. Am J Physiol Endocrinol Metab 289 (2005), 703-709; Butler et al. Diabetes 52 (2003), 2304-2314; Hoppener et al. Diabetologia 42(4) (1999), 427-434; and Janson et al. Proc. Natl. Acad. Sci. USA 93(14) (1996), 7283-7288; compared to the here described mouse model. In addition, the mouse model of the present invention showed an appearance of extracellular amyloid deposits at 2-month of age and extensive amyloidosis observed at 4-month of age, with associated β-cell loss, in comparison to the previously described mouse models where minimal amyloid deposition were observed in mice spontaneously developing diabetes, as well as showed an extracellular amyloid deposition at 12 months of age (amyloid severity=1 to 5% and amyloid prevalence=40 to 60%), with associated β-cell loss, and showed extracellular amyloid deposition at 16 to 19 months of age (amyloid prevalence=25 to 85%), with associated β-cell loss; see e.g. Hull et al. Diabetes 52(2) (2003), 372-379; Hull et al. Am J Physiol Endocrinol Metab 289 (2005), 703-709; Hoppener et al. Diabetologia 42(4) (1999), 427-434.

The novel features of the mouse model with respect to previous models (see review: Matveyenko et al. (2006), ILAR J. 47(3): 225-233) include:

1) Different genetic background:
   Our mouse model: hemizygous hIAPP transgenics under a FVB/NxDBA/2J background.
   Previously described mouse models: hemizygous hIAPP transgenics under FVB/N (Couce et al. (1996), Diabetes 45: 1094-1101), FVB/N/A$^{vy}$/A (Soeller et al. (1998), Diabetes 47: 743-750), C57BL/6J (Hull et al. (2005), Am J Physiol Endocrinol Metab 289: 703-709), DBA/2J (Hull et al. (2005), Am J Physiol Endocrinol Metab 289: 703-709), C57BL/6JxDBA/2J (Hull et al. (2003), Diabetes 52(2): 372-379; Hull et al. (2005), Am J Physiol Endocrinol Metab 289: 703-709), C57BL/6J/A$^{vy}$/A (Butler et al. (2003), Diabetes 52: 2304-2314), and ob/ob (Hoppener et al. (1999), Diabetologia 42(4): 427-434) background. Homozygous hIAPP transgenics under a FVB/N background (Janson et al. (1996), Proc. Natl. Acad. Sci. USA 93(14): 7283-7288).

2) Early-onset metabolic phenotype:
Our mouse model: mice spontaneously develop diabetes characterized by impaired glucose tolerance and hyperglycemia already present at 1-month and 2-month of age, respectively.
Previously described mouse models:
mice do not spontaneously develop diabetes: hemizygous hIAPP transgenics under FVB/N (Couce et al. (1996), Diabetes 45: 1094-1101), C57BL/6J (Hull et al. (2005), Am J Physiol Endocrinol Metab 289: 703-709), and DBA/2J background (Hull et al. (2005), Am J Physiol Endocrinol Metab 289: 703-709).
mice spontaneously develop diabetes with hyperglycemia and impaired glucose tolerance by 6 to 10 months of age: hemizygous hIAPP transgenics under FVB/N/A$^{vy}$/A (Soeller et al. (1998), Diabetes 47: 743-750), C57BL/6J/A$^{vy}$/A (Butler et al. (2003), Diabetes 52: 2304-2314), C57BL/6JxDBA/2J (Hull et al. (2003), Diabetes 52(2): 372-379; Hull et al. (2005), Am J Physiol Endocrinol Metab 289: 703-709) and ob/ob background (Hoppener et al. (1999), Diabetologia 42(4): 427-434).

3) Early onset and more prominent islet pathology:
Our mouse model: appearance of extracellular amyloid deposits at 2-month of age and extensive amyloidosis observed at 4-month of age, with associated β-cell loss.
Previously described mouse models: minimal amyloid deposition observed in mice spontaneously developing diabetes. Hemizygous hIAPP transgenics under C57BL/6JxDBA/2J background (Hull et al. (2003), Diabetes 52(2): 372-379; Hull et al. (2005), Am J Physiol Endocrinol Metab 289: 703-709) showed extracellular amyloid deposition at 12 months of age (amyloid severity=1 to 5% and amyloid prevalence=40 to 60%), with associated β-cell loss. Hemizygous hIAPP transgenics under ob/ob background (Hoppener et al. (1999), Diabetologia 42(4): 427-434) showed extracellular amyloid deposition at 16 to 19 months of age (amyloid prevalence=25 to 85%), with associated β-cell loss.

Mice were kept in a 12 h light schedule and given normal chow diet consisting (as a percentage of total calories [kcal]) of 7% fat and 18% protein (KLIBA NAFAG). All mice had free access to food and water.

Rats

Hemizygous transgenic rats with islet β-cell expression of hIAPP driven by the rat insulin II promoter (Matveyenko et al., Diabetes (2009), 1604-1615; Butler et al., Diabetes (2004), 1509-1516) and wild-type Sprague-Dawley male rats were obtained from Charles River Laboratories (Germany) Rats were kept in a 12 h light schedule and given normal chow diet. All rats had free access to food and water.

Treatment

Transgenic mice received a once-weekly administration of recombinant mouse chimeric IgG2a antibody NI-203.26C11-ch (10 mg/kg body weight; i.p.) starting at 4 weeks of age and for the duration of the study. Vehicle-treated transgenic and wild-type mice were intraperitoneally administered with physiological saline (PBS).

Transgenic and wild-type rats received a once-weekly administration of recombinant rat chimeric IgG2b antibody NI-203.26C11-r (3 mg/kg body weight; i.p.) starting at 12 weeks of age and for the duration of the study. Vehicle-treated transgenic and wild-type rats were intraperitoneally administered with physiological saline (PBS).

Oral Glucose Tolerance Test, Fasting Blood Glucose, Plasma Insulin and Plasma hIAPP For glucose tolerance testing, 5 hour-fasted mice and overnight-fasted rats were orally administered with a 2 g/kg glucose solution. Blood samples were collected from the mouse tail vein before and 10, 30, 60, 120 and 240 min after glucose injection. Rat blood was collected from the sublingual vein and under gas anesthesia before and 30, 60, 120 and 240 min after glucose injection. Blood glucose was measured using a glucometer (CONTOUR XT sensors, Bayer). Fasting blood glucose was measured from blood samples collected after overnight fasting. Non-fasting plasma insulin and hIAPP levels were determined using a mouse insulin (Mercodia) and a human amylin (Millipore) enzyme-linked immunosorbent assay (ELISA) kit.

Histology

Mice were sacrificed and pancreases were dissected, weighted (to calculate pancreatic mass), fixed in 4% (wt/vol.) phosphate-buffered paraformaldehyde, embedded in paraffin and 3-μm sections were cut. Paraffin-embedded human tissues were obtained from the University Hospital Basel (UHB, Basel, Switzerland) and 3-μm sections were cut. Sections were stained with 0.1% (wt/vol.) thioflavin S to visualize amyloid deposits, polyclonal guinea pig anti-insulin antibody (1:3; FLEX; Dako), mouse monoclonal anti-IAPP antibody (1:100; R10/99; Abcam), polyclonal rabbit anti-glucagon antibody, and recombinant NI-203.26C11 (human or mouse chimeric) antibody. Following primary antibody, slices were incubated with TRITC-conjugated donkey anti-guinea pig antibody (Jackson ImmunoResearch Europe Ltd., UK), Cy5-conjugated or biotinylated donkey anti-mouse antibody, Cy5-conjugated goat anti-rabbit antibody, Cy5-conjugated or biotinylated donkey anti-human antibody. Streptavidin-biotin-peroxidase reaction (Vectastain ABC kit, Vector Lab Inc., Burlingame, USA) was used with biotinylated secondary antibodies and sections were counterstained with hematoxylin to visualize cell nuclei Image analysis was performed using Image J software. To quantify ThioS-positive amyloid area, insulin-positive area, mean islet area and islet density, all islets per pancreatic section (five sections per animal) were examined in detail at 20× magnification. ThioS-positive amyloid area and insulin-positive area were computed as the areas corresponding to fluorescence above a preset threshold. Islet area was determined by manually outlining the islet visualized on the ThioS channel, where the outline of the islet is clearly visible. ThioS staining was expressed in relation to the pancreas area and the insulin area. Insulin staining was expressed in relation to the pancreas area and the islet area.

Statistical Analysis

Data are expressed as means±SEM. Significant differences between pairs of groups were determined using Student's t test. Glucose tolerance data were analyzed using a repeated-measures ANOVA (with time on study and treatment as independent variables). All statistical analyses were conducted using Prism software (GraphPad Software Inc., San Diego, Calif., USA). $p<0.05$ was considered significant.

Example 1: Validation of Affinity and Selectivity of the Antibodies for Pathological hIAPP in Human Tissue To test whether the NI-203.26C11 antibody selectively and dose-dependently recognizes pathological hIAPP aggregates human tissue, i.e. in the pancreas of patients diagnosed with type 2 diabetes mellitus (T2D), paraffin-embedded pancreas sections of patients diagnosed with T2D showing amyloid load in pancreatic islets observed upon ThioS staining (subject 1 and 2) were tested for NI-203.26C11 antibody binding. As control paraffin-embedded pancreas sections of a patients not diagnosed with T2D (subject 3 and 4) were used (FIG. 2).

After formic acid pretreatment, sections were incubated with the NI-203.26C11-ch antibody at different concentrations, i.e. 1 nM, 3 nM, 10 nM, and 30 nM, or a mouse monoclonal anti-IAPP antibody (1:100; Abcam, Cambridge, UK) and secondary donkey anti-mouse antibody were used as control, followed by incubation with biotinylated donkey anti-human secondary antibody (1:500; Jackson ImmunoResearch, Newmarket, UK) or biotinylated goat anti-mouse secondary antibody (1:500; Jackson ImmunoResearch, Newmarket, UK). Antibody signal was amplified with the Vectastain ABC-AP kit (Vector Laboratories, USA) and detected with diaminobenzidine substrate (Thermo Fisher Scientific, USA). Upon avidin/biotin blocking (Avidin/Biotin blocking kit, Vector Laboratories, USA), pancreatic islet β-cells were visualized using a polyclonal guinea pig anti-insulin antibody (1:5; Dako, USA) coupled to a biotinylated donkey anti-guinea pig secondary antibody (1:500; Jackson ImmunoResearch Laboratories, USA) and antibody signal was amplified with the Vectastain ABC-Aβ kit (Vector Laboratories, USA) and detected with alkaline phosphatase substrate (Vector Laboratories, USA).

NI-203.26C11 antibody showed dose-dependent a staining in T2D pancreatic islets loaded with islet amyloids (subjects 1 and 2) but not in healthy control pancreatic islets lacking islet amyloids (subjects 3 and 4) (FIG. 2). However, NI-203.26C11 antibody did not recognize physiological hIAPP on healthy control pancreases, as shown in FIG. 2 two lower rows.

Figure 3:
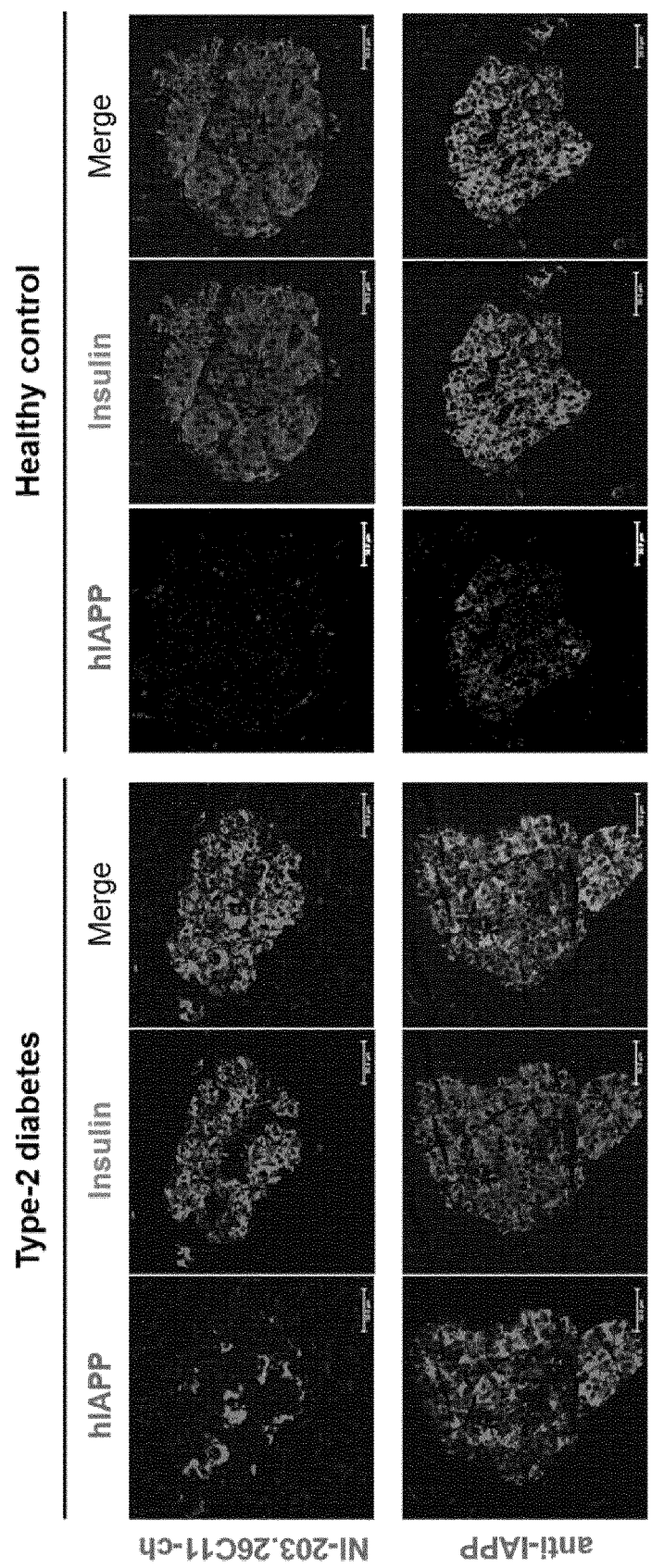
FIG. 3: NI-203.26C11 antibody selectively recognizes pathological hIAPP aggregates in T2D patients. NI-203.26C11 antibody shows a staining in T2D pancreatic islets but does not recognize physiological IAPP on healthy control pancreatic islets lacking pathological hIAPP aggregates. Detection of hIAPP aggregates on T2D pancreatic islets with recombinant mouse chimeric antibody NI-203.26C11 (NI-203.26C11-ch; blue; 100 nM; top panels). NI-203.26C11 staining of hIAPP aggregates is restricted to islet areas deprived of β-cells (no merge with insulin staining in red). Detection of insulin on islet β-cells with anti-insulin antibody (1:3; red). Anti-IAPP antibody (1:100; anti-IAPP; bottom panels) recognizes physiological hIAPP on T2D and healthy control pancreatic islet β-cells, as shown by co-localization with insulin staining (merge with insulin staining in red). Scale bars: 50 µm.

In addition, the selectivity of the NI-203.26C11 antibody was tested by an immunofluorescence staining (FIG. 3). Tissue sections were labeled against IAPP and pancreatic islet β-cells utilizing NI-203.26C11 antibody, mouse monoclonal anti-IAPP antibody (1:100; Abcam, Cambridge, UK) and secondary donkey anti-mouse antibody, and polyclonal guinea pig anti-insulin antibody (1:5; Dako, USA) for pancreatic islet β-cells. The visualization was performed with fluorescently labeled secondary antibodies.

In brief, paraffin-embedded sections were labeled with NI-203.26C11 or mouse monoclonal anti-IAPP antibody (1:100; Abcam, Cambridge, UK) and subsequently by Cy5-labeled secondary donkey anti-mouse IgG. Pancreatic islet β-cells, i.e. insulin, colocalization with IAPP was determined using a polyclonal guinea pig anti-insulin antibody (1:5; Dako, USA) coupled to a TRITC-labeled donkey anti-guinea pig secondary antibody (1:500; Jackson ImmunoResearch Laboratories, USA). Stained samples were cover-slipped with Tris-buffered glycerol (a 3:7 mixture of 0.1 M Tris-HCl at pH 9.5 and glycerol supplemented with 50 mg/mL n-propyl-gallate).

As result, the recombinant mouse chimeric antibody NI-203.26C11 (NI-203.26C11-ch; blue; 100 nM; FIG. 3 top panels) detected hIAPP aggregates on T2D pancreatic islets. In particular, the staining was restricted to islet areas deprived of β-cells (no merge with insulin staining in red). However, no staining was visible on physiological IAPP in healthy control pancreatic islets lacking pathological hIAPP aggregates.

Figure 4:
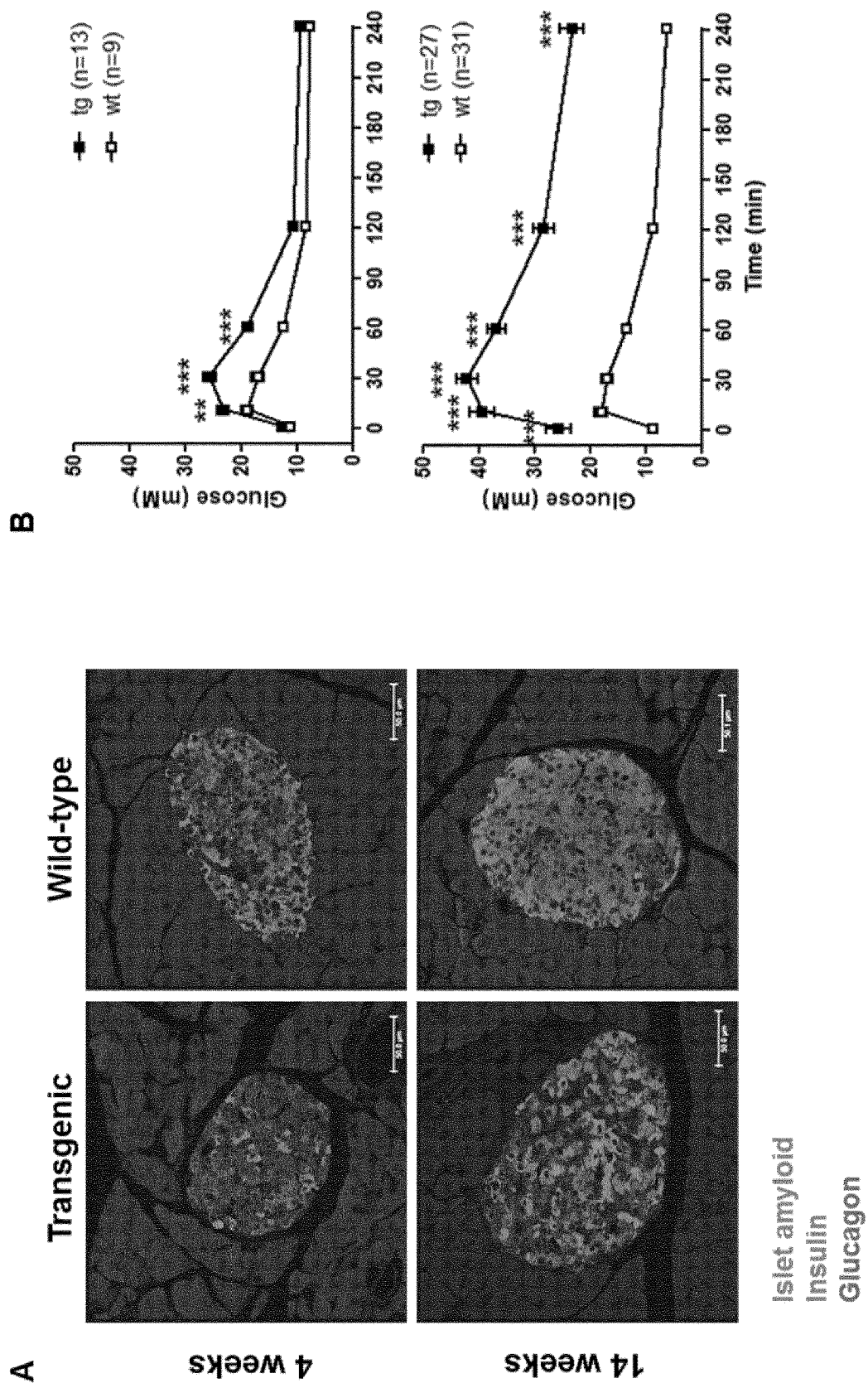
FIG. 4: Impaired glucose tolerance precedes the deposition of islet amyloids in a transgenic mouse model of type-2 diabetes (hIAPP transgenic mice). (A) Islet amyloids are visualized at 14 weeks of age but not 4 weeks of age in hIAPP transgenic mice. Wild-type mice are deprived of islet amyloids. Representative images of hIAPP transgenic and wild-type mouse pancreatic islets stained for islet amyloids (0.1% ThioS), insulin (anti-insulin antibody; 1:3; red) and glucagon (anti-glucagon antibody; 1:2500; blue). (B) Impaired glucose tolerance in 4 week- and 14 week-old transgenic mice. Blood glucose levels during an oral glucose tolerance test (oGTT) performed in hIAPP transgenic and wild-type mice at 4 weeks (top panel) and 14 weeks (bottom panel) of age. Blood glucose levels after oral glucose were higher in hIAPP transgenic mice compared with wild-type mice at 4 weeks (tg, n=13; wt, n=9) and 14 weeks of age (tg, n=27; wt, n=31). Fasting blood glucose levels were similar among groups at 4 weeks but increased in hIAPP transgenic mice at 14 weeks of age.  p<0.01 and * p<0.001 compared with wt group. Scale bar: 50 µm.

Example 2: Impaired Glucose Tolerance Precedes the Deposition of ThioS-Positive Material in a Transgenic Mouse Model of Type-2 Diabetes To test the deposition of islet amyloids in the transgenic mouse model, islet amyloids were visualized utilizing an immunofluorescence staining, as described above utilizing hIAPP transgenic and wild-type mouse pancreatic islets stained for islet amyloids (0.1% ThioS), insulin (anti-insulin antibody; 1:3; red) and glucagon (anti-glucagon antibody; 1:2500; blue), at 14 weeks of age but not 4 weeks of age in hIAPP transgenic mice, see FIG. 4. As shown in FIG. 4(A) the wild-type mice were deprived of islet amyloids compared to the transgenic mice.

In addition the glucose tolerance was measured in the transgenic mice, see FIG. 4(B). In brief, glucose was administered intraperitoneally to a 5-hour fasting animal at 2 mg per gram of bodyweight and then the glucose level in the blood (peripheral blood, blood glucose concentration) of the animal was determined every 15 minutes over 240 minutes using a commercial measuring apparatus (Medisafe Reader, Terumo Co., Ltd.). The measurement utilizing a commercial measuring apparatus is based on colorimetric analysis. A measuring chip is prepared, and onto the chip are placed glucose oxidase and peroxidase as catalysts and 4-aminoantipyrine and N-ethyl-N(2-hydroxy-3-sulfopropyl)-m-toluidine as chromogenic agents. When a blood sample absorbed through capillary phenomenon is placed on this chip, here 4 µl, and then glucose in the blood is oxidized by glucose oxidase. Then, the chromogenic agents on the chip are oxidized by hydrogen peroxide generated at this moment and peroxidase, which yields a red-purple color. The amount of glucose in the blood is calculated by measuring the degree of this color tone. The oral glucose tolerance test was performed in transgenic and wild-type mice at 4 weeks (top panel) and 14 weeks (bottom panel) of age, see FIG. 4(B). The results showed that blood glucose levels after oral glucose were higher in hIAPP transgenic mice compared with wild-type mice at 4 weeks (tg, n=13; wt, n=9) and 14 weeks of age (tg, n=27; wt, n=31). In addition, the fasting blood glucose levels were similar among groups at 4 weeks but increased in hIAPP transgenic mice at 14 weeks of age.

Figure 5:
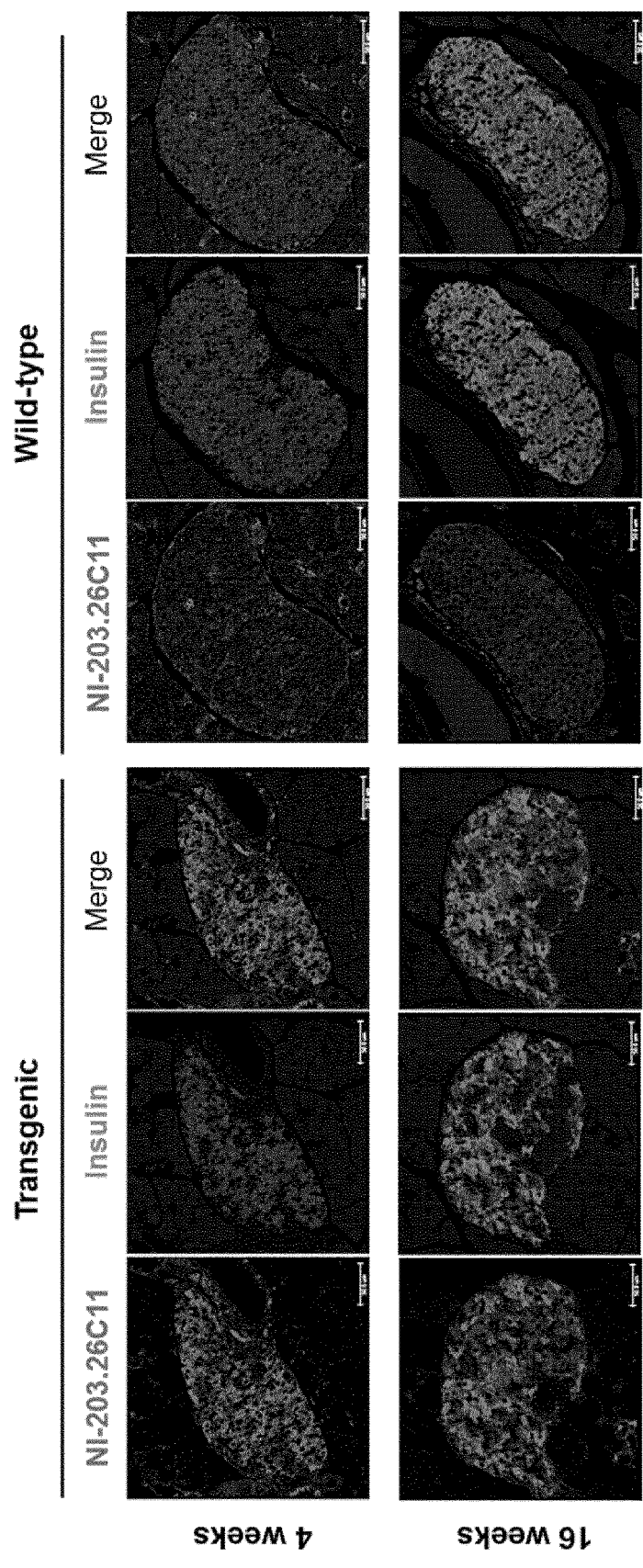
FIG. 5: NI-203.26C11 antibody selectively binds hIAPP aggregates in hIAPP transgenic mice. NI-203.26C11 shows a staining on pancreatic islets of 4 week- and 16 week-old hIAPP transgenic mice (blue staining; left panels), with no staining on age-matched wild-type mice (absence of blue staining; right panels). Detection of hIAPP aggregates on transgenic islets with recombinant human antibody NI-203.26C11 (NI-203.26C11; blue; 100 nM). Detection of insulin on islet β-cells with anti-insulin antibody (1:3; red). Scale bar: 50 µm.

Example 3: Validation of Affinity and Selectivity of the Antibodies for hIAPP Aggregates in hIAPP Transgenic Mice To test the affinity and selectivity of the NI-203.26C11 antibody against hIAPP aggregates in hIAPP transgenic mice, immunofluorescence and immunohistochemical analysis utilizing recombinant human antibody NI-203.26C11 (NI-203.26C11; blue; 100 nM) for detection of hIAPP aggregates on transgenic islets and anti-insulin antibody (1:3; red) for the detection of insulin on islet β-cells, were performed, see FIG. 5. The results showed a NI-203.26C11 staining on pancreatic islets in 4 week- and 16 week-old hIAPP transgenic mice (blue staining; left panels, FIG. 5), with no staining on age-matched wild-type mice (absence of blue staining; right panels FIG. 5).

Figure 6:
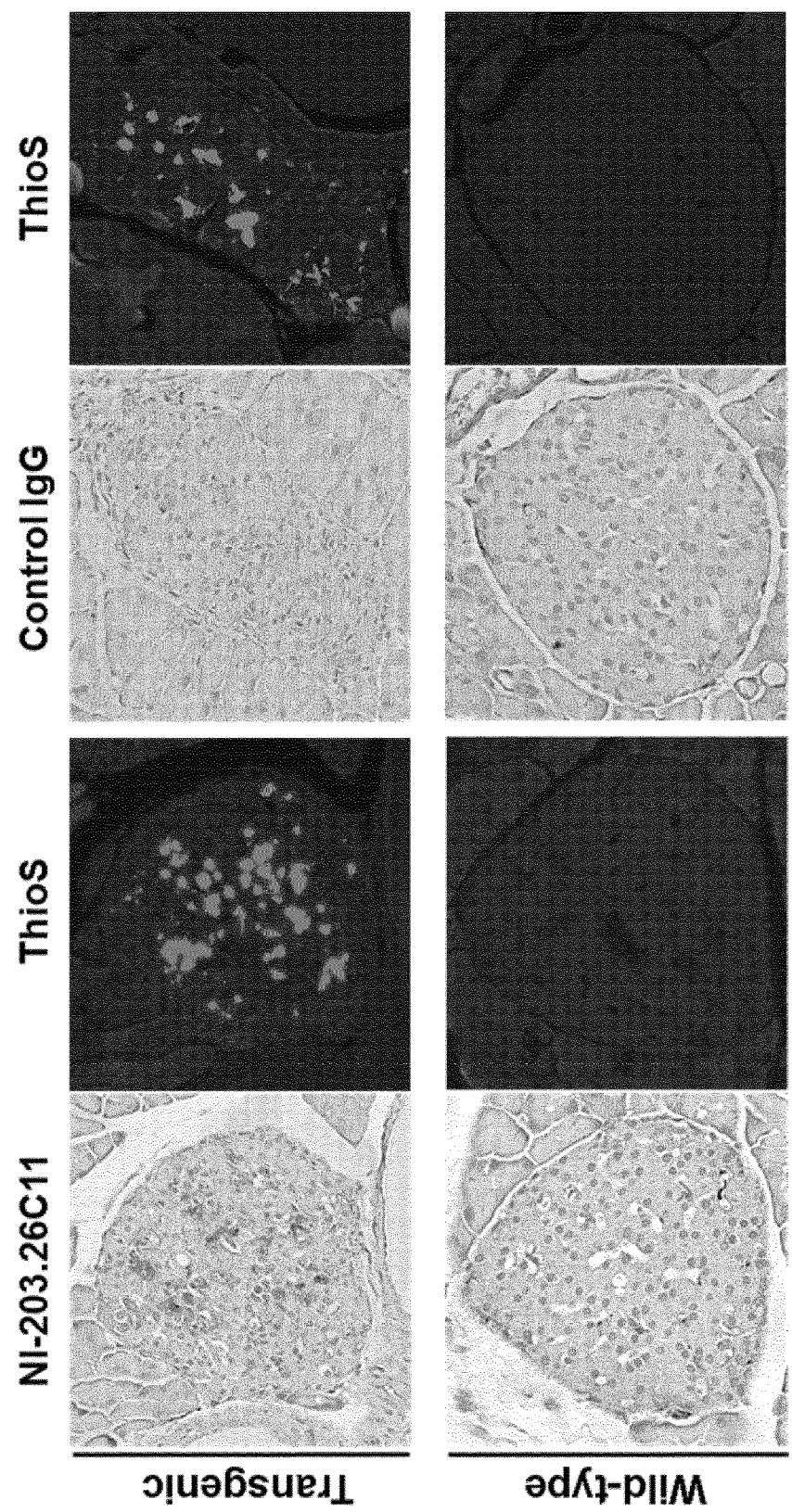
FIG. 6: NI-203.26C11 antibody targets aggregated hIAPP after a single administration in hIAPP transgenic mice. Recombinant human NI-203.26C11 or isotype control (control IgG) antibodies were administered to 16 week-old hIAPP transgenic and wild-type mice at 10 mg/kg (i.p.) and antibody binding was evaluated 2 days after administration using an anti-human secondary antibody. Recombinant human NI-203.26C11 (brown staining here) targets transgenic islets showing ThioS-positive amyloids (green staining here) but not ThioS-negative wild-type islets. No staining was observed with the control IgG. Counterstaining was performed to visualize cell nuclei (faint blue i.o., faint staining here).

Additionally, the NI-203.26C11 antibody was administered to 16 week-old hIAPP transgenic and wild-type mice at a single administration (10 mg/kg (i.p.)) and its binding was evaluated 2 days after administration using an anti-human secondary antibody, see FIG. 6.

It was shown that the recombinant human NI-203.26C11 (brown staining, FIG. 6) targets transgenic islets showing ThioS-positive amyloids (green staining, FIG. 6) but not ThioS-negative wild-type islets. In addition, no staining was observed with the control IgG.

Example 4: Administration of the Antibodies of the Present Invention Protects Against β-Cell Loss in hIAPP Transgenic Mice To test the effect of the NI-203.26C11 on β-cells in hIAPP transgenic mice, pancreatic insulin, islet area, and insulin secretion was measured after a once-weekly treatment with recombinant mouse chimeric NI-203.26C11 antibody in hIAPP transgenic mice (tg NI-203.26C11-ch, n=23; 10 mg/kg i.p. for 12 weeks); see FIG. 7.

In brief, paraffin-embedded sections were labeled with polyclonal guinea pig anti-insulin antibody (1:5; Dako, USA) and subsequently by TRITC-labeled donkey anti-guinea pig secondary antibody (1:500; Jackson ImmunoResearch Laboratories, USA). Stained samples were coverslipped with Tris-buffered glycerol (a 3:7 mixture of 0.1 M Tris-HCl at pH 9.5 and glycerol supplemented with 50 mg/mL n-propyl-gallate). Quantification of the insulin-positive area in relation to the pancreas and islet area, mean islet area and islet density is described in the methods section.

Figure 7:
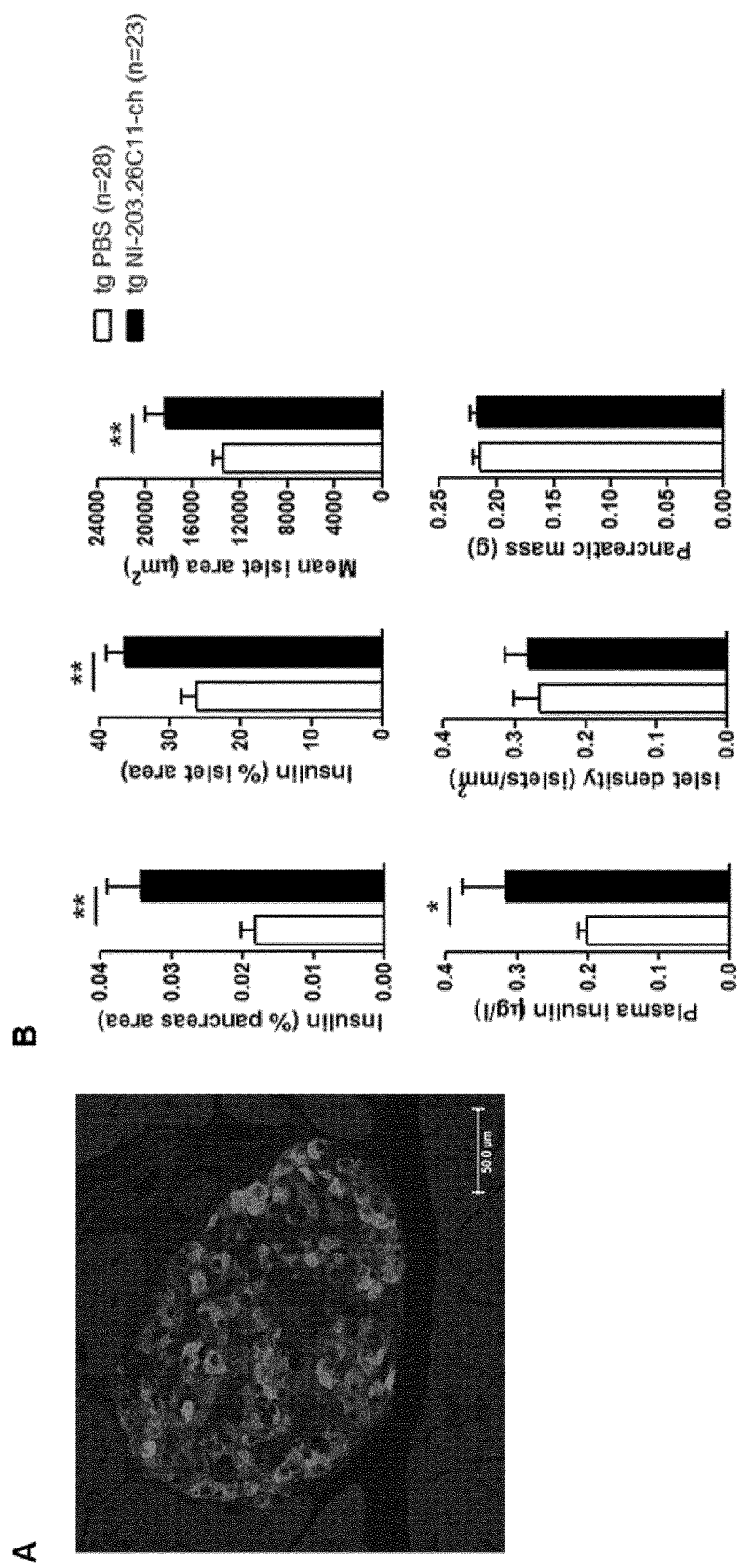
FIG. 7: NI-203.26C11 antibody protects against β-cell loss in hIAPP transgenic mice. (A) Representative image of a mouse pancreatic islet stained with anti-insulin antibody to visualize β-cells (red i.o., strong staining here). (B) Once-weekly treatment with recombinant mouse chimeric NI-203.26C11 antibody in hIAPP transgenic mice (tg NI-203.26C11-ch, n=23; 10 mg/kg i.p. for 12 weeks) increases pancreatic insulin (insulin-positive area in % pancreas area and % islet area; top left and top middle panels), islet area (mean islet area; top right panel) and insulin secretion (plasma insulin levels; bottom left panel) compared with hIAPP transgenic mice receiving PBS (tg PBS, n=28). Islet density and pancreatic mass were unchanged after NI-203.26C11-ch treatment (bottom middle and bottom right panel, respectively). * p<0.05 and ** p<0.01 compared with tg PBS group. Scale bar: 50 µm.

The results showed pancreatic insulin (insulin-positive area in % pancreas area and % islet area; top left and top middle panels), islet area (mean islet area; top right panel) and insulin secretion (plasma insulin levels; bottom left panel) was increased compared with hIAPP transgenic mice receiving PBS (tg PBS, n=28). However, the islet density and pancreatic mass were unchanged after NI-203.26C11-ch treatment (bottom middle and bottom right panel, respectively; FIG. 7).

Figure 9:
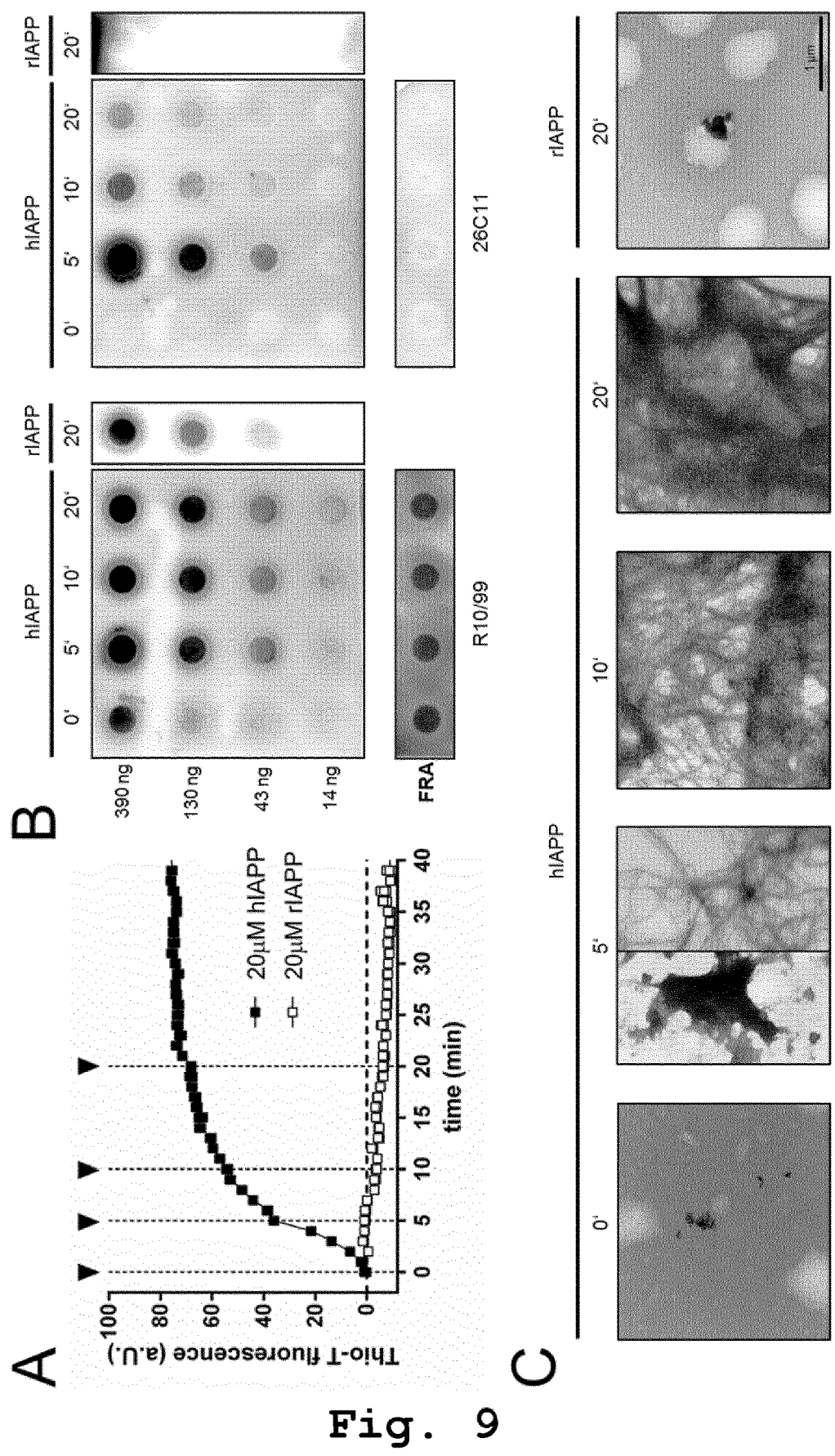
FIG. 9: NI-203.26C11 recognizes predominantly early fibrillar hIAPP aggregate species. (A) Thioflavin-T (Thio-T) aggregation assay with a classical sigmoidal aggregation curve for hIAPP (■) but no aggregation for rodent IAPP (□; rIAPP). (B) Dotblot analysis of samples (1:3 dilution series) taken from the Thio-T experiment at the time points indicated revealed unselective binding of anti-IAPP antibody to all hIAPP samples collected as well as to rIAPP taken after 20 min. In contrast, NI-203.26C11 displayed a selective binding for hIAPP preparations taken at the growth phase of hIAPP aggregation (5'), with decreased binding to hIAPP samples taken at later time points (10' and 20'). Importantly, NI-203.26C11 remained immuno-negative for non-aggregated hIAPP fractions (0') and did not react to rIAPP. In filter retardation assay (FRA), the anti-IAPP antibody recognized SDS-resistant fibrillar hIAPP species at all time-points assessed, whereas no reactivity could be seen for NI-203.26C11 against these hIAPP species. (C) Transmission electron microscopy (TEM) analysis of samples taken from the Thio-T aggregation assay revealed a diverse morphological spectrum. No large fibrillar aggregates could be detected for hIAPP taken before aggregation (0') neither for rIAPP taken at late stage (20'). Intermediate hIAPP species showed both, amorphous non-fibrillar as well as fibrillar characteristics (5') while samples taken at the border to (10') or within the equilibrium phase (20') predominantly showed a fibrillar morphology.

Example 5: Antibody of the Present Invention Recognizes Predominantly Early Fibrillary IAPP To test to which hIAPP aggregate species the antibody NI-203.26C11 binds, a Thioflavin-T (Thio-T) aggregation assay was performed. In brief, spontaneous aggregation of synthetic hIAPP was assessed by monitoring amyloid fibril formation via the increase of fluorescence of the amyloid-specific dye Thioflavin-T (Thio-T). Lyophilized synthetic hIAPP peptide (Bachem, Switzerland) was reconstituted in pure DMSO and mixed in Thio-T solution (20 µM Thio-T in 20 mM Tris-HCl, pH 8.5) to a final peptide concentration of 20 µM. After filtration through a 0.22 µm filter (Millipore), aggregation solution was immediately transferred into fluorescence quartz cuvettes and aggregation was recorded under stirring on a Cary Eclipse Fluorescence spectrophotometer (Agilent) measuring the fluorescence emission wavelength at 489 nm (excitation at 456 nm) every 1 min at RT. The assay showed a classical sigmoidal aggregation curve for hIAPP, but not for rodent IAPP (rIAPP) as shown in FIG. 9 A.

Additionally, a DotBlot analysis were performed utilizing samples from the Thio-T experiment. The DotBlot analysis was performed as follows, hIAPP preparations from aggregation assays were serially diluted and filtered through a PBS-T (0.1% Tween-20 in PBS) pre-equilibrated nitrocellulose membrane (pore size 0.1 µm). Wells were washed with PBS-T and samples were added. After complete filtration the membrane was washed three times. Subsequently, the membrane was shortly air-dried for 15 min at RT, incubated in blocking buffer (3% BSA, 0.1% Tween-20 in PBS) for 1 h at RT, and incubated with mouse-chimeric NI-203.26C11 antibody (5 µg/ml in blocking buffer) for 1 h at RT. As control antibody, a chicken anti-IAPP antibody (1:1000; P10997, Agrisera) was used. After washing, the membrane was incubated with HRP-conjugated anti-mouse and anti-chicken IgG secondary antibodies (1:10000 dilution; Jackson ImmunoResearch Laboratories) for 1 h at RT. Conversion of HRP substrate (ECL) was analyzed using ImageQuant LAS 4000 detection (GE Healthcare). As shown in FIG. 9 B a selective binding for hIAPP preparations in early phases of the hIAPP aggregation could be shown, while a decreased binding was observed in later phases of growth. However, the antibody NI-203.26C11 remained immuno-negative for non-aggregated hIAPP fractions (0') and did not react to rIAPP.

Furthermore, filter retardation assays (FRA) were performed using hIAPP preparation from aggregation assays mixed in 2% SDS. Samples were then filtered through a cellulose acetate membrane and membrane was blocked with blocking buffer (3% milk, 0.1% Tween-20 in PBS) for 1 h at RT. Detection of SDS resistant hIAPP assemblies was done as described for the DotBlot analysis. The FRA showed that the anti-IAPP antibody recognize SDS-resistant fibrillar hIAPP species at all time-points assessed, whereas no reactivity could be observed for the antibody NI-203.26C11 against these hIAPP species, see e.g. FIG. 9 B.

Morphology of hIAPP assemblies was assessed by Transmission electron microscopy (TEM) analysis. In brief, samples were adsorbed on glow-discharged carbon-coated copper grids and excess of sample was removed by blotting on filter paper. Grids were stained with 2% (w/v) uranyl acetate for 60 sec and excess of solution was removed by washing with ddH20. After air-drying, grids were imaged with a Philips CM100 transmission electron microscope with an acceleration voltage of 100 kV. As shown in FIG. 9 C a diverse morphological spectrum could be assessed with TEM. In particular, at time point 0 min which indicates the time point before aggregation, no large fibrillar aggregates. After 5 min amorphous non-fibrillar as well as fibrillar characteristics could be observed. A fibrillar morphology was observed in samples taken at later time points, i.e. 10 min and 20 min.

Figure 8:
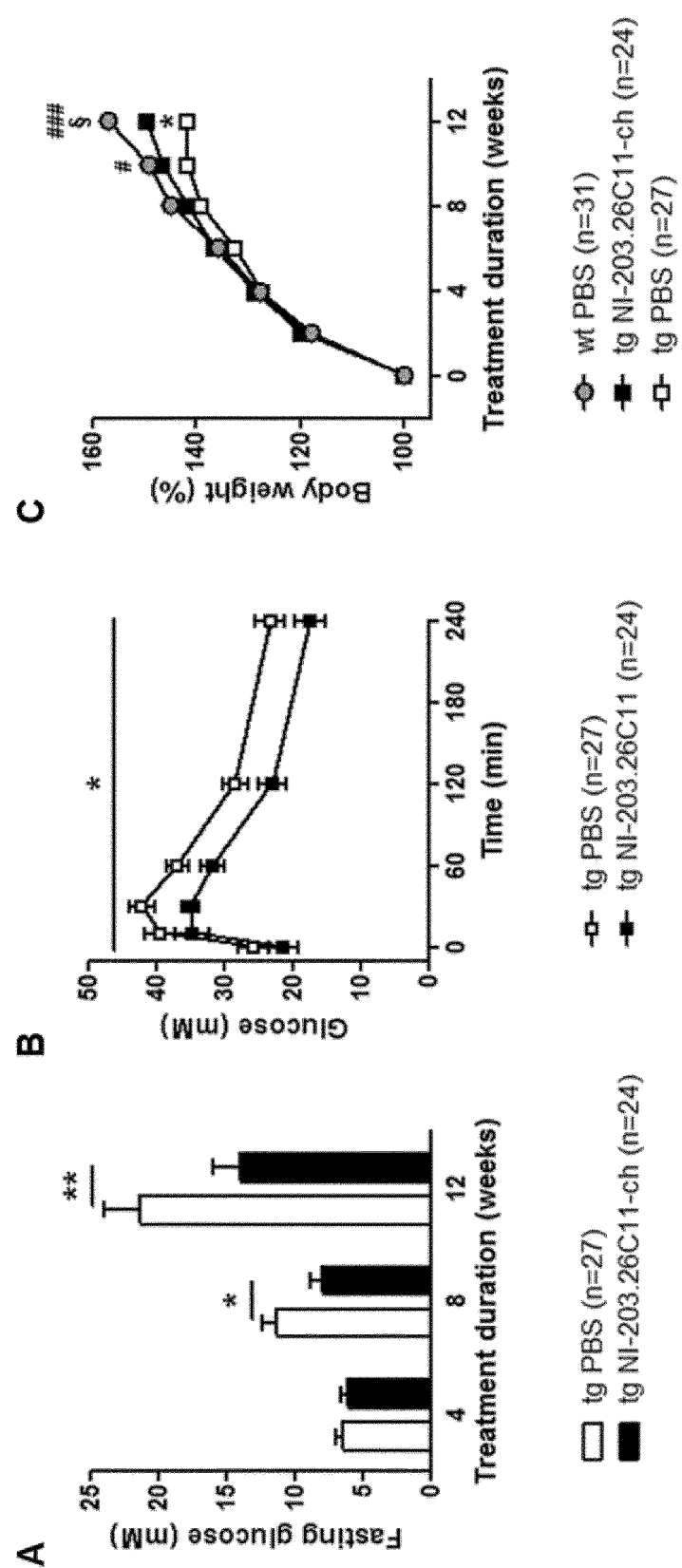
FIG. 8: NI-203.26C11 antibody decreases fasting blood glucose, improves glucose tolerance and normalizes body weight gain in hIAPP transgenic mice. Recombinant mouse chimeric NI-203.26C11 antibody was administered once-weekly to hIAPP transgenic mice (tg NI-203.26C11-ch, n=24; 10 mg/kg i.p.). PBS was used as vehicle (tg PBS, n=27). (A) NI-203.26C11 antibody significantly decreases fasting blood glucose after 8 and 12 weeks of treatment in hIAPP transgenic mice compared with PBS group. Blood glucose levels were measured after overnight fasting. (B) NI-203.26C11 antibody significantly improves glucose tolerance in hIAPP transgenic mice compared with PBS group. Blood glucose levels during an oral glucose tolerance test (oGTT) performed in hIAPP transgenic mice after 10 weeks of treatment. (C) Incremental body weight (%) was normalized in NI-203.26C11-treated hIAPP transgenic mice over 12 weeks of treatment, as compared with wild-type mice injected with PBS (wt PBS, n=31). hIAPP transgenic mice under PBS treatment showed impaired body weight gain compared with wild-type mice. tg NI-203.26C11-ch compared with tg PBS: * $p<0.05$ and ** $p<0.01$; tg PBS compared with wt PBS: # $p<0.05$ and ### $p<0.001$; tg NI-203.26C11-ch compared with wt PBS: § $p<0.05$.

Example 6: Administration of the Antibodies of the Present Invention Prevents from Symptoms Associated with Diabetes To proof whether the administration of NI-203.26C11 antibody can improve symptoms associated with diabetes, the recombinant mouse chimeric NI-203.26C11 antibody was administered once-weekly to hIAPP transgenic mice (tg NI-203.26C11-ch, n=24; 10 mg/kg i.p.) and the blood glucose, glucose tolerance, body weight was assessed as already described above; see FIG. 8.

After 8 and 12 weeks of treatment the NI-203.26C11 antibody showed a significant decrease of fasting blood glucose measured after overnight fasting in hIAPP transgenic mice compared with PBS group. In addition, the glucose tolerance after 10 weeks of treatment was significant improved.

Furthermore, a normalized body weight could be observed in hIAPP transgenic mice treated with NI-203.26C11, i.e. incremental body weight (%) was normalized in NI-203.26C11-treated over 12 weeks of treatment, as compared with wild-type mice injected with PBS (wt PBS, n=31). In particular, hIAPP transgenic mice under PBS treatment showed impaired body weight gain compared with wild-type mice; see FIG. 8.

Therefore, as a result it has been shown that NI-203.26C11 antibody decreases fasting blood glucose, improves glucose tolerance and normalizes body weight gain in hIAPP transgenic mice.

Example 7: Antibodies of the Present Invention Normalize Glucose Tolerance in a hIAPP Transgenic Rat In addition to further improve the results shown in transgenic mice, the effects of NI-203.26C11 antibody in a transgenic rat model of type-2 diabetes (hIAPP transgenic rats) were assessed, see FIG. 10. In particular, a recombinant rat chimeric NI-203.26C11 antibody was administered once-weekly to hIAPP transgenic rats (tg NI-203.26C11-r, n=9; 3 mg/kg i.p.) and wild-type rats (wt NI-203.26C11-r, n=4; 3 mg/kg i.p.).

To test the glucose tolerance, an oral glucose tolerance (oGTT) test was performed before treatment in 3 month-old hIAPP transgenic rats and wild-type rats showing equivalent blood glucose levels. As a result, the NI-203.26C11-r antibody normalized blood glucose levels in hIAPP transgenic rats during an oGTT performed after 8 weeks of treatment, as compared with PBS-treated hIAPP transgenic rats (tg PBS, n=10) and PBS-treated wild-type rats (wt PBS, n=5). Additionally it was shown that the NI-203.26C11-r antibody does not affect blood glucose levels in wild-type rats (wt NI-203.26C11-r).

The invention claimed is:

1. A method of restoring human islet amyloid polypeptide hIAPP induced impaired glucose tolerance and normalizing blood glucose level comprising administering to a subject in need thereof an effective amount of an antibody or hIAPP-binding fragment thereof, wherein the antibody or hIAPP-binding fragment thereof comprises an hIAPP-binding domain comprising:
   (i) a heavy chain variable (VH) region comprising the three complementarity determining regions (CDRs) of the heavy chain variable (VH) sequence of SEQ ID NO: 2 (as depicted in FIG. 1); and
   (ii) a light chain variable (VL) region comprising the amino acid sequence of SEQ ID NO: 6.

2. The method of claim 1, wherein the antibody or hIAPP-binding fragment thereof is used for normalizing body weight gain.

3. The method of claim 1, wherein the subject is at risk of developing diabetes mellitus type 2 (T2D) and/or hypertension.

4. The method of claim 1, wherein the heavy chain variable region comprises the amino acid sequence of SEQ ID NO:2.

5. The method of claim 1, wherein the antibody or hIAPP-binding fragment thereof comprises a polypeptide sequence which is heterologous to the hIAPP-binding domain.

6. The method of claim 1, wherein the antibody or hIAPP-binding fragment thereof comprises a constant domain or part thereof which is heterologous to the hIAPP-binding domain.

7. The method of claim 6, wherein the constant domain is of the IgG type.

8. The method of claim 7, wherein the constant domain is of the IgG1 class or isotype.

9. The method of claim 6, wherein the constant domain is a human constant domain.

10. The method of claim 1, wherein the antibody or hIAPP-binding fragment thereof is
(a) detectably labeled or
(b) attached to a drug.

11. The method of claim 10, wherein the detectable label is selected from the group consisting of an enzyme, a radioisotope, a fluorophore, and a heavy metal.

12. The method of claim 1, wherein the antibody or hIAPP-binding fragment thereof is formulated in a pharmaceutical composition.

13. The method of claim 12, wherein the composition further comprises an agent capable of preventing or reducing IAPP amyloid formation.

14. The method of claim 13, wherein the agent is selected from the group consisting of flavonoids, IAPP analogs, metformin, and thiazolidinediones, such as rosiglitazone.

15. The method of claim 12, further comprising a pharmaceutically acceptable carrier.

16. The method of claim 12, wherein the antibody or hIAPP-binding fragment thereof is administered subcutaneously (s.c.), intramuscularly (i.m.), or intravenously (i.v.).

17. The method of claim 12, wherein the antibody or hIAPP-binding fragment thereof is administered on a weekly, biweekly, or monthly basis.

18. The method of claim 1, wherein the administering is before onset of islet amyloid fibrils, protofibrils, or amyloid plaque in pancreatic tissue.

19. The method of claim 1, wherein the antibody or hIAPP-binding fragment thereof is administered at a dosage of about 10 mg/kg in a transgenic hIAPP mouse model and/or about 3 mg/kg in a transgenic hIAPP animal model.

20. The method of claim 19, wherein the transgenic hIAPP animal model is characterized by being capable of expressing at least one transgene comprising a DNA sequence encoding a human islet amyloid polypeptide (hIAPP), and
(i) spontaneously developing diabetes characterized by impaired glucose tolerance and/or hyperglycemia at about 1-month and 2-month of age, respectively; or
(ii) appearance of extracellular amyloid deposits at about 2-month of age and/or extensive amyloidosis associated β-cell loss at about 4-month of age.

21. The method of claim 20, wherein the transgenic hIAPP animal model is hemizygous or the DNA sequence is operably linked to the rat insulin II promoter.

22. The method of claim 19, wherein the transgenic hIAPP animal model is a rat model.

23. The method of claim 1, wherein the antibody or hIAPP-binding fragment thereof selectively binds aggregated hIAPP in pancreas tissue of a human diabetic subject.

24. The method of claim 1, wherein the antibody is a human-derived monoclonal antibody.

* * * * *

```
                          SEQUENCE LISTING

<160> NUMBER OF SEQ ID NOS: 7

<210> SEQ ID NO 1
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-203.26C11-VH variable heavy chain (VH)
      sequence
<220> FEATURE:
<221> NAME/KEY: V_region
<222> LOCATION: (76)..(111)
<223> OTHER INFORMATION: complementarity determining region (CDR)
      VH-CDR1
<220> FEATURE:
<221> NAME/KEY: V_region
<222> LOCATION: (154)..(201)
<223> OTHER INFORMATION: complementarity determining region (CDR)
      VH-CDR2
<220> FEATURE:
<221> NAME/KEY: V_region
<222> LOCATION: (298)..(330)
<223> OTHER INFORMATION: complementarity determining region (CDR)
      VH-CDR3

<400> SEQUENCE: 1 cag gtg cag ctg cag gag tcg ggc cca gga ttg gtg aag cct tct cag         48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt         96
Thr Leu Ser Leu Thr Cys Thr Val Ser Gly Gly Ser Ile Ser Ser Gly
                20                  25                  30 aat tac tac tgg acc tgg atc cgg cag ccc gcc ggg aag gga ctg gag        144
Asn Tyr Tyr Trp Thr Trp Ile Arg Gln Pro Ala Gly Lys Gly Leu Glu
            35                  40                  45 tgg att ggg cat atc tat tcc agt ggg acc acc aat tac aac ccc tcc        192
Trp Ile Gly His Ile Tyr Ser Ser Gly Thr Thr Asn Tyr Asn Pro Ser
        50                  55                  60 ctc gag agt cga gtc acc att tca gta gac acg tcc aag aac cag ttc        240
Leu Glu Ser Arg Val Thr Ile Ser Val Asp Thr Ser Lys Asn Gln Phe
65                  70                  75                  80 tcc ctg agc ctg aac tct gtg acc gcc gca gac acg gcc gtt tat tac        288
Ser Leu Ser Leu Asn Ser Val Thr Ala Ala Asp Thr Ala Val Tyr Tyr
                85                  90                  95 tgt gcg aga cca ctg gct aca gtt ccg gat gct ttt aat atc tgg ggc        336
Cys Ala Arg Pro Leu Ala Thr Val Pro Asp Ala Phe Asn Ile Trp Gly
                100                 105                 110 caa ggg aca atg gtc acc gtc tct tcg                                    363
Gln Gly Thr Met Val Thr Val Ser Ser
```

<210> SEQ ID NO 2
<211> LENGTH: 121
<212> TYPE: PRT
<213> ORGANISM: Homo sapiens

<400> SEQUENCE: 2

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asn Tyr Tyr Trp Thr Trp Ile Arg Gln Pro Ala Gly Lys Gly Leu Glu
        35                  40                  45

Trp Ile Gly His Ile Tyr Ser Ser Gly Thr Thr Asn Tyr Asn Pro Ser
    50                  55                  60

Leu Glu Ser Arg Val Thr Ile Ser Val Asp Thr Ser Lys Asn Gln Phe
65                  70                  75                  80

Ser Leu Ser Leu Asn Ser Val Thr Ala Ala Asp Thr Ala Val Tyr Tyr
                85                  90                  95

Cys Ala Arg Pro Leu Ala Thr Val Pro Asp Ala Phe Asn Ile Trp Gly
            100                 105                 110

Gln Gly Thr Met Val Thr Val Ser Ser
        115                 120
```

<210> SEQ ID NO 3
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-203.26C11-VK variable kappa-light chain (VK)
      sequence
<220> FEATURE:
<221> NAME/KEY: V_region
<222> LOCATION: (70)..(114)
<223> OTHER INFORMATION: complementarity determining region (CDR)
      VK-CDR1
<220> FEATURE:
<221> NAME/KEY: V_region
<222> LOCATION: (160)..(180)
<223> OTHER INFORMATION: complementarity determining region (CDR)
      VK-CDR2
<220> FEATURE:
<221> NAME/KEY: V_region
<222> LOCATION: (277)..(303)
<223> OTHER INFORMATION: complementarity determining region (CDR)
      VK-CDR3

<400> SEQUENCE: 3

```
gaa att gtg atg act cag tct cca gac tcc ctg gct gtg tct ctg ggc    48
Glu Ile Val Met Thr Gln Ser Pro Asp Ser Leu Ala Val Ser Leu Gly
1               5                   10                  15 gag agg gcc acc atc aag tgc aag tcc agc cag agt gtt tta tac agc    96
Glu Arg Ala Thr Ile Lys Cys Lys Ser Ser Gln Ser Val Leu Tyr Ser
            20                  25                  30 aat aag aac ttc tta gct tgg tac cag cag aaa cca gga cag cct cct   144
Asn Lys Asn Phe Leu Ala Trp Tyr Gln Gln Lys Pro Gly Gln Pro Pro
        35                  40                  45 aaa tta ctc att tac tgg gca tct act cgg gaa tcc ggg gtc cct gac   192
Lys Leu Leu Ile Tyr Trp Ala Ser Thr Arg Glu Ser Gly Val Pro Asp
    50                  55                  60 cga ttc agt ggc agc ggg tct ggg aca gat ttc act ctc acc atc agc   240
Arg Phe Ser Gly Ser Gly Ser Gly Thr Asp Phe Thr Leu Thr Ile Ser
```

```
Arg Phe Ser Gly Ser Gly Ser Gly Thr Asp Phe Thr Leu Thr Ile Ser
 65                  70                  75                  80 agc ctg cag gct gaa gat gtg gca gtt tat tac tgt cag cag tat tat      288
Ser Leu Gln Ala Glu Asp Val Ala Val Tyr Tyr Cys Gln Gln Tyr Tyr
                 85                  90                  95 agt aat cct aac act ttt ggc cag ggg acc aag gtg gag atc aaa          333
Ser Asn Pro Asn Thr Phe Gly Gln Gly Thr Lys Val Glu Ile Lys
            100                 105                 110

<210> SEQ ID NO 4
<211> LENGTH: 111
<212> TYPE: PRT
<213> ORGANISM: Homo sapiens

<400> SEQUENCE: 4

Glu Ile Val Met Thr Gln Ser Pro Asp Ser Leu Ala Val Ser Leu Gly
  1               5                  10                  15

Glu Arg Ala Thr Ile Lys Cys Lys Ser Ser Gln Ser Val Leu Tyr Ser
             20                  25                  30

Asn Lys Asn Phe Leu Ala Trp Tyr Gln Gln Lys Pro Gly Gln Pro Pro
         35                  40                  45

Lys Leu Leu Ile Tyr Trp Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Tyr Tyr
                 85                  90                  95

Ser Asn Pro Asn Thr Phe Gly Gln Gly Thr Lys Val Glu Ile Lys
            100                 105                 110

<210> SEQ ID NO 5
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-203.26C11-VK PIMC variable kappa-light chain
      (VK) sequence
<220> FEATURE:
<221> NAME/KEY: V_region
<222> LOCATION: (70)..(114)
<223> OTHER INFORMATION: complementarity determining region (CDR)
      VK-CDR1
<220> FEATURE:
<221> NAME/KEY: V_region
<222> LOCATION: (160)..(180)
<223> OTHER INFORMATION: complementarity determining region (CDR)
      VK-CDR2
<220> FEATURE:
<221> NAME/KEY: V_region
<222> LOCATION: (277)..(303)
<223> OTHER INFORMATION: complementarity determining region (CDR)
      VK-CDR3

<400> SEQUENCE: 5 gat att gtg atg act caa tca cca gac tcc ctg gct gtg tct ctg ggc       48
Asp Ile Val Met Thr Gln Ser Pro Asp Ser Leu Ala Val Ser Leu Gly
  1               5                  10                  15 gag agg gcc acc atc aag tgc aag tcc agc cag agt gtt tta tac agc       96
Glu Arg Ala Thr Ile Lys Cys Lys Ser Ser Gln Ser Val Leu Tyr Ser
             20                  25                  30 aat aag aac ttc tta gct tgg tac cag cag aaa cca gga cag cct cct      144
Asn Lys Asn Phe Leu Ala Trp Tyr Gln Gln Lys Pro Gly Gln Pro Pro
         35                  40                  45
```

```
aaa tta ctc att tac tgg gca tct act cgg gaa tcc ggg gtc cct gac      192
Lys Leu Leu Ile Tyr Trp Ala Ser Thr Arg Glu Ser Gly Val Pro Asp
    50                  55                  60 cga ttc agt ggc agc ggg tct ggg aca gat ttc act ctc acc atc agc      240
Arg Phe Ser Gly Ser Gly Ser Gly Thr Asp Phe Thr Leu Thr Ile Ser
65                  70                  75                  80 agc ctg cag gct gaa gat gtg gca gtt tat tac tgt cag cag tat tat      288
Ser Leu Gln Ala Glu Asp Val Ala Val Tyr Tyr Cys Gln Gln Tyr Tyr
                85                  90                  95 agt aat cct aac act ttt ggc cag ggg acc aag ctg gag atc aag          333
Ser Asn Pro Asn Thr Phe Gly Gln Gly Thr Lys Leu Glu Ile Lys
                100                 105                 110

<210> SEQ ID NO 6
<211> LENGTH: 111
<212> TYPE: PRT
<213> ORGANISM: Homo sapiens

<400> SEQUENCE: 6

Asp Ile Val Met Thr Gln Ser Pro Asp Ser Leu Ala Val Ser Leu Gly
1               5                   10                  15

Glu Arg Ala Thr Ile Lys Cys Lys Ser Ser Gln Ser Val Leu Tyr Ser
            20                  25                  30

Asn Lys Asn Phe Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Ser Asn Pro Asn Thr Phe Gly Gln Gly Thr Lys Leu Glu Ile Lys
                100                 105                 110

<210> SEQ ID NO 7
<211> LENGTH: 7
<212> TYPE: PRT
<213> ORGANISM: Artificial Sequence
<220> FEATURE:
<223> OTHER INFORMATION: unique linear epitope recognized by antibody
      NI-203.26C11 aa 2 to 8

<400> SEQUENCE: 7

Cys Asn Thr Ala Thr Cys Ala
1               5
```